(12) United States Patent
Olivas et al.

(10) Patent No.: US 6,486,385 B1
(45) Date of Patent: Nov. 26, 2002

(54) LETTUCE VARIETY ICON

(75) Inventors: Nathan K. Olivas, Salinas, CA (US); Nathan J. Olivas, Salinas, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 09/862,211

(22) Filed: May 21, 2001

Related U.S. Application Data

(60) Provisional application No. 60/206,549, filed on May 24, 2000.

(51) Int. Cl.[7] .............................. A01H 4/00; A01H 1/00; A01H 5/00; A01H 5/10; A01H 5/12
(52) U.S. Cl. ...................... 800/305; 800/260; 800/265; 800/295; 800/298; 435/410; 435/430.1
(58) Field of Search .............................. 800/305, 260, 800/265, 295, 298; 435/410, 430.1

(56) References Cited

PUBLICATIONS

Waycott et al. 1995. Photoperiodic response of genetically diverse lettuce accessions. J. Amer. Soc. Hort. Sci. 120(3):460–467.*

* cited by examiner

*Primary Examiner*—David T. Fox
*Assistant Examiner*—Francis Moonan
(74) *Attorney, Agent, or Firm*—Morrison & Foerster LLP

(57) ABSTRACT

A new lettuce variety designated Icon is described. Icon is an iceberg lettuce variety exhibiting stability and uniformity. Icon seeds are deposited with the American Type Culture Collection and have ATCC deposit number PTA-4011.

7 Claims, 1 Drawing Sheet

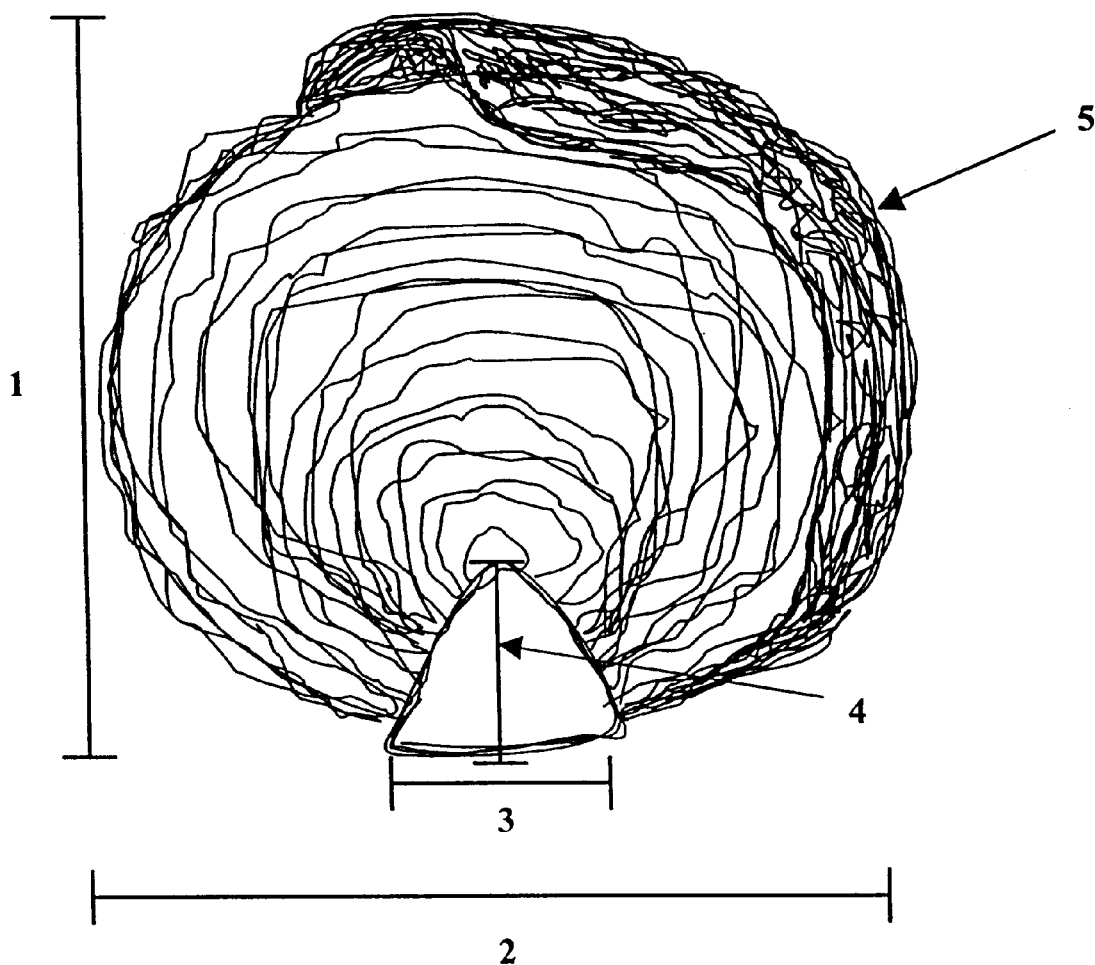
FIGURE 1: Sliced Iceberg Lettuce

LETTUCE VARIETY ICON

I. RELATED APPLICATION

This application claims the benefit under 35 U.S.C. §119 (e) of U.S. provisional patent application No. 60/206,549 filed May 24, 2000 which is hereby incorporated by reference in its entirety.

II. FIELD OF THE INVENTION

This invention relates to the field of plant breeding. In particular, this invention relates to a new lettuce, *Lactuca saliva*, variety, Icon.

III. BACKGROUND OF THE INVENTION

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

IV. SUMMARY OF THE INVENTION

In order to meet these needs, the present invention is directed to an improved iceberg lettuce variety that exhibits vigorous growth, increased weight and yield. In particular, the present invention is directed to lettuce, *Lactuca sativa*, seed designated as Icon having ATCC Accession Number PTA-401 1. The present invention is further directed to a lettuce, *Lactuca sativa* plant produced by growing Icon lettuce seed having ATCC Accession Number PTA-4011. The present invention is further directed to a *Lactuca sativa* plant having all the physiological and morphological characteristics of a *Lactuca sativa* plant produced by growing Icon lettuce seed having ATCC Accession Number PTA-4011. The present invention is further directed to an $F_1$ hybrid lettuce, *Lactuca sativa* plant having Icon as a parent wherein Icon is grown from Icon lettuce seed having ATCC Accession Number PTA-4011.

The present invention is further directed to pollen and ovules isolated from Icon lettuce plants. The present invention is further directed to tissue culture of Icon lettuce plants.

The present invention is further directed to a method of selecting lettuce plants comprising a) growing Icon lettuce plants wherein the Icon plants are grown from lettuce seed having ATCC Accession Number PTA-4011 and b) selecting a progeny plant from step a) wherein the progeny plant is phenotypically distinguishable from the parent plant. The present invention is further directed to lettuce plants and seeds produced by the lettuce plants wherein the lettuce plants are isolated by the selection method of the invention.

The present invention is further directed to a method of breeding lettuce plants comprising crossing a lettuce plant with a plant grown from Icon lettuce seed having ATCC Accession Number PTA-40 11. The present invention is further directed to lettuce plants and seeds produced therefrom where the lettuce plant is isolated by the breeding method of the invention.

V. BRIEF DESCRIPTION OF THE DRAWING

The invention will be better understood by reference to FIG. 1 which shows a drawing of a cross-section of an iceberg lettuce head showing head length 1, head diameter 2, core diameter 3, core length 4, and a wrapper leaf 5. In the description that follows, head length, head diameter, core diameter, core length, and wrapper leaf are described without associated reference numbers, but are intended to correspond to the respective reference numbers listed above.

VI. BRIEF DESCRIPTION OF THE TABLES

The invention will be better understood by reference to the Tables in which;

Table 1 shows trial data comparing Icon and Spector iceberg lettuce varieties.

Table 2 shows trial data comparing Icon and Pybas 251 iceberg lettuce varieties.

Table 3 shows trial data comparing Icon and Spector iceberg lettuce varieties.

Table 4 shows trial data comparing Icon and Pybas 251 iceberg lettuce varieties.

Table 5 shows trial data comparing Icon and Spector iceberg lettuce varieties.

Table 6 shows trial data comparing Icon and Pybas 251 iceberg lettuce varieties.

Table 7 shows trial data comparing Spector and Icon iceberg lettuce varieties.

Table 8 shows trial data comparing Pybas 251 and Icon iceberg lettuce varieties.

Table 9 shows trial data comparing Icon and Pybas iceberg lettuce varieties.

Table 10 shows trial data comparing Pybas 251 and Icon iceberg lettuce varieties.

Table 11 shows trial data comparing Spector and Icon iceberg Lettuce Varieties.

Table 12 shows trial data comparing Icon and Spector iceberg lettuce varieties.

Table 13 shows trial data comparing Icon and Desert Spring iceberg lettuce varieties.

Table 14 shows trial data comparing Icon and Desert Spring iceberg lettuce varieties.

Table 15 shows trial data comparing Icon and Desert Spring iceberg lettuce varieties.

Table 16 shows trial data comparing Icon and Spector iceberg lettuce varieties.

Table 17 shows trial data comparing Icon and Spector iceberg lettuce varieties.

Table 18 shows bolting data comparing Icon, Pybas 251 and Spector iceberg lettuce varieties.

VII. DETAILED DESCRIPTION OF THE INVENTION

In order to more clearly understand the invention, the following definitions are provided:

Iceberg Lettuce: Iceberg lettuce, *Lactuca sativa* L. var. capitala L. is also known as 'crisp head' lettuce. Iceberg lettuce is a lettuce plant type that forms a firm, spherical head formed with tightly folded brittle textured foliage as illustrated in FIG. 1. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length: Core length is the length of the internal lettuce stem. Core length is measured from the base of the cut head to the tip of the core.

Core Diameter: Core diameter is the diameter of the lettuce stem at the base of the cut head.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf Average Head Diameter: Average head diameter is an average of the measured head diameter and head length of the lettuce head.

Average Head Diameter: Core Length Ratio. The ratio of the average head diameter to core length is indicative of the percentage of useable product produced by the lettuce plant.

Frame Diameter: The frame diameter is a measurement of the lettuce plant diameter at its widest point. The measurement of frame diameter is from the outer most wrapper leaf tip to outer most wrapper leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of an iceberg lettuce variety, a lettuce head at market state when the head is solid and has reached an adequate size and weight.

Taking into account these definitions, the present invention is directed to seeds of the lettuce variety Icon, plants produced by growing Icon lettuce seeds, plants selected from a collection of Icon plants and seeds derived or produced therefrom; plants produced by crossing a lettuce plant with an Icon lettuce plant and seeds derived or produced therefrom.

VIII. ORIGIN AND BREEDING HISTORY OF THE VARIETY ICON

Icon is an iceberg lettuce variety developed from a hand pollinated cross of Pybas 251 available from Pybas Seed Co. and Spector available from Genecorp Seed made in year 1 in the San Joaquin Valley. The two parental varieties were selected for their compatibility. Pybas 251 was selected for its large head and frame size and cold tolerance. Spector was selected for its dark color, good texture and heading characteristics. The cross was made to produce a dark green, large heading iceberg lettuce with improved texture for early winter plantings in Yuma Ariz., and the mid winter plantings in the Salinas Valley of Calif. F1 seed was harvested.

Approximately 40 plants of the F1 seed were planted in a San Joaquin Valley research production field for seed increase in year 2. The block was rogued, eliminating the self pollinating plants. The F2 seed was harvested in August of year 2.

The F2 seed was evaluated in research and development plot trials late in year 2 and throughout year 3. The seed was increased in year 3 in a San Joaquin Valley research production field. Individual plant selections were made. Plants were selected for improved head and frame size, dark green color and a smoother texture. Additional rogueing of the block for uniformity in size and maturity was done until complete seed maturity. The remaining plants were bulk harvested producing the F3 seed in the fall of year 3.

The F3 seed was extensively trialed throughout the year 4 growing season in Yuma, Ariz. and the Salinas Valley of Calif., and was designated as PX 621. The seed was increased in year 4 in the San Joaquin Valley research production, selecting for large head and frame size, dark green color and an improved smoother texture. Further rogueing for size, type and maturity was done until harvest of the F4 seed. The resulting plants were noted as stable and expressing the desired phenotypic traits.

The F4 seed was evaluated in research and development plot trials during year 4 and 5 growing seasons in the winter plantings of Yuma, Ariz. and the Salinas Valley of Calif., where it exhibited good uniformity. The F4 seed was increased in year 5 in a San Joaquin Valley research production field and selectively rogued for uniformity of type, size and maturity. The F5 seed was then harvested.

During the year 5 and 6 growing seasons, the F5 seed was trialed in Yuma Ariz. and the Salinas Valley of Calif. This variety was noted to exhibit the desired phenotypic traits, producing an improved large dark head and frame, while being uniform, stable and without variants. The F5 seed was planted in year 6 in a San Joaquin Valley commercial production field. It was selectively rogued for uniformity in size and maturity. The F6 seed was harvested that fall.

The F6 seed was planted in large strip trials in year 6 and year 7 growing seasons of Yuma, Ariz. and the Salinas Valley of Calif. The evaluation of these trials showed the variety to exhibit the desired phenotypic characteristics of improved head and frame size, dark green color, and improved texture, while being uniform, stable and without variants. The F6 seed was increased in year 7 in a San Joaquin Valley commercial production field, and selectively rogued for uniformity in size and maturity. The F7 seed was harvested.

Icon, as evaluated in commercial trails and production, has been stable and without variants for two generations.

*Lactuca sativa* cultivar Icon has numerous distinguishing characteristics as outlined in the following summary.

A. Variety Description Information

| Plant Type: | Iceberg |
|---|---|
| Seed: | |
| Seed Color: | Black |
| Light Dormancy: | Light not required |
| Heat Dormancy: | Susceptible |
| Cotyledons: | |
| Shape of Cotyledons: | Intermediate |
| Shape of Fourth Leaf: | Broad/Elongated |
| Length/Width Index of Fourth Leaf: | 26 |
| Apical Margin: | Finely Dentate |
| Basal Margin: | Finely Dentate |
| Undulation: | Flat |
| Green Color: | Dark Green |
| Anthocyanin: | |
| Distribution: | Absent |
| Rolling: | Absent |
| Cupping: | Absent |
| Reflexing: | Lateral Margins |
| Mature Leaves: | |
| Margin: | |
| Incision Depth (Deepest penetration of the margin): | Moderate |

-continued

| Plant Type: | Iceberg |
|---|---|
| Indentation (Finest Division of the Margin): | Crenate |
| Undulation of the Apical Margin: | Moderate |
| Green Color: | Dark |
| Anthocyanin Distribution: | Absent |
| Size: | Large |
| Glossiness: | Moderate |
| Blistering: | Slight/moderate |
| Leaf Thickness: | Intermediate |
| Trichomes: | Absent |

B. Comparison to Parent Line

| Characteristic | Icon | Pybas 251 |
|---|---|---|
| Spread of Frame Leaves | 50 cm | 51 cm |
| Head Diameter (market trimmed with single cup leaf) | 16 | 16 |
| Head Shape | Spherical | Slightly elongated |
| Head Size Class | Large | Large |
| Head Count per Carton | 24 | 24 |
| Head Weight | 863 | 889 |
| Head Firmness | Firm | Firm |
| Butt | | |
| Shape | Round | Round/Pointed |
| Midrib | Moderately Raised | Moderately Raised |
| Core (Stem of Market-trimmed Head) | | |
| Diameter at the base of the Head | 36 mm | 36 mm |
| Ratio of Head Diameter/Core Diameter | 4.4 | 4.4 |
| Core Height from base of Head to Apex | 42 | 42 |
| Number of Days from First Water Date to Seed Stalk Emergence (Summer condition) | 59 | 57 |
| Bolting Class | Medium | Medium |
| Height of Mature Seed Stalk | 110 | 117 |
| Spread of Bolter Plant | 38 | 34 |
| Bolter Leaves | Curved | Curved |
| Margin | Dentate | Dentate |
| Color | Medium Green | Medium Green |
| Bolter Habit | | |
| Terminal Inflorescence | Present | Present |
| Lateral Shoots (above head) | Present | Present |
| Basal Side Shoots | Absent | Absent |
| Adaptation Regions | | |

C. Growing Season

| Season | Icon | Pybas 251 |
|---|---|---|
| Spring area | Salinas Valley | Salinas Valley |
| Summer area | Salinas Valley | NA |
| Fall area | Salinas Valley | Salinas Valley |
| Winter area | Yuma Az | NA |

D. Diseases and Stress Reactions

| Disease or Stress | Icon | Pybas 251 |
|---|---|---|
| Virus | NA | NA |
| Big Vein: | NA | NA |
| Lettuce Mosaic: | NA | NA |
| Cucumber Mosaic: | NA | NA |
| Broad Bean Wilt: | NA | NA |
| Turnip Mosaic: | NA | NA |
| Best Western Yellows: | NA | NA |
| Lettuce Infectious Yellows: | NA | NA |

E. Fungi/Bacteria

| Fungal/Bacterial | Icon | Pybas 251 |
|---|---|---|
| Corky Root Rot (Pythium Root Rot): | NA | NA |
| Downy Mildew (Races I, IIA, III): | NA | NA |
| Powdery Mildew: | NA | NA |
| Sclerotinia Rot: | NA | NA |
| Bacterial Soft Rot (Pseudomonas spp. & others): Not tested | | |
| Botrytis (Gray Mold): | NA | NA |
| Other: Corky Root Rot (Rhizomonas suberifaciens): | NA | NA |

F. Insects

| Insects | Icon | Pybas 251 |
|---|---|---|
| Cabbage Loopers: | NA | NA |
| Root Aphids: | NA | NA |
| Green Peach Aphid: | NA | NA |

G. Physiological/Stress

| Stress | Icon | Pybas 251 |
|---|---|---|
| Tipburn | NA | NA |
| Heat | NA | NA |
| Drought | NA | NA |
| Cold | Tolerant | Tolerant |
| Salt | NA | NA |

H. Post Harvest

| Characteristic | Icon | Pybas 251 |
| --- | --- | --- |
| Pink Rib | NA | NA |
| Russet Spotting | NA | NA |
| Rusty Brown Discoloration | NA | NA |
| Internal Rib Necrosis (Blackheart, Gray Rib, Gray Streak) | NA | NA |
| Brown Stain | NA | NA |

Breeding and Selection

The present invention is further directed to the use of Icon lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color and texture of the lettuce head. Crosses are made, for example, to produce a dark green, sure heading iceberg lettuce with improved texture, and size for fall plantings in Yuma Ariz., and Huron Calif.

To optimize crossing, it is important to note that lettuce is an obligate self-pollinating species. This means that the pollen is shed before stigma emergence, assuring 100% self-fertilization. Since each lettuce flower is an aggregate of about 10–20 individual florets (typical of the Compositae family), manual removal of the anther tubes containing the pollen may be performed by procedures well known in the art of lettuce breeding.

In addition to manual removal of anther tubes, a modified method of misting to wash the pollen off prior to fertilization may be used to assure crossing or hybridization. About 60–90 min past sunrise, flowers to be used for crossings are selected. The basis for selection are open flowers, with the stigma emerged and the pollen visibly attached to the single stigma (about 10–20 stigma). Using 3–4 pumps of water from a regular spray bottle, the pollen are washed off with enough pressure to dislodge the pollen grains, but not enough to damage the style. Excess water is dried off with clean paper towels. About 30 min later the styles should spring back up and the two lobes of the stigma are visibly open in a "V" shape. Pollen from another variety or donor parent are then introduced by gently rubbing the stigma and style of the donor parent to the maternal parent. Tags with the pertinent information on date and pedigree are then secured to the flowers.

About 2–3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two useful references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907–908 both of which are hereby incorporated by reference in their entirety.

B. Selection

In addition to crossing, selection may be used to isolate lettuce new lettuce lines. In lettuce selection, one or more lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determined if they exhibit the desired characteristics from the originally selected line. Selection work is continued over multiple generations to increase the uniformity new line.

IX. DEPOSIT INFORMATION

Applicants have made available to the public without restriction a deposit of at least 2500 seeds of lettuce variety Icon with the American Type Culture Collection (ATCC), Rockville, Md. 20852 on Jan. 24, 2001, which has been assigned ATCC number PTA-4011.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

X. EXAMPLES

Example 1

General Trialing Method

I. Set Up

The following steps illustrate the general trialing method of the invention.

1. A trial is set up to compare one or more lines. Parental lines and competing varieties are identified.
2. Primary slots are identified.
3. Necessary accession lines are located and purchased/obtained from seed dealers or growers.
4. All varieties are assigned a number to maintain integrity and anonymity.
5. Trials are set up in with all necessary varieties. Variety arrangement for trial is diagramed.

II. Planting

1. Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance

1. All tested varieties are treated identically. Plants are watered, fertilized, and treated to control pests in the same manner as other lettuce plants in the commercial field.
2. The trial is thinned to separate the plants for optimum growth.

IV. Evaluation

1. Evaluations are done as near to the time of the commercial harvest as possible.
2. The evaluation is conducted "blindly". The evaluator(s) do not have the key to the trial at the time of evaluation.
3. 24 heads of each variety are evaluated.
   a. The frame diameter of 24 random plants are measured to the nearest cm.

b. 24 mature heads of each variety are cut to the cap leaf.
c. The heads are carried to an adequate work station
d. The following measurements are then conducted and recorded:
   1. Each head is weighed to the nearest gram.
   2. The core diameter of each head is measured to the nearest mm.
   3. The heads are then sliced in to halves, discarding 1 half.
   4. The core lengths (from the cut stem to the core tip) are measured to the nearest mm.
   5. The head length (from the cut stem to the cap leaf) is measured to the nearest mm.
   6. The head diameter (at its widest point) is measured to the nearest mm.
   7. The ideal maturity or harvest date is then estimated based on the solidity of the head, the core length and any other physiological characteristics present.
   8. The leaf color is documented using the Munsell Color Charts for Plant Tissue.
e. From these measurements, an Excel program is used to calculate the averages, the standard deviations and the T-Tests for the compared varieties.

Example 2

Comparative Analysis

Following the procedures of Example 1, Icon iceberg lettuce was compared to various other varieties. Comparative data was obtained and analyzed for different iceberg lettuce lines. Core length, core diameter, head diameter, head length, average head diameter, frame diameter and head weight as provided in the definitions section above and FIG. 1 were compared. The data are presented in Tables 1–18.

Table 1 shows trial data comparing Icon and Spector iceberg lettuce varieties. Table 2 shows trial data comparing Icon and Pybas 251 iceberg lettuce varieties. Table 3 shows trial data comparing Icon and Spector iceberg lettuce varieties. Table 4 shows trial data comparing Icon and Pybas 251 iceberg lettuce varieties. Table 5 shows trial data comparing Icon and Spector iceberg lettuce varieties. Table 6 shows trial data comparing Icon and Pybas 251 iceberg lettuce varieties. Table 7 shows trial data comparing Spector and Icon iceberg lettuce varieties. Table 8 shows trial data comparing Pybas 251 and Icon iceberg lettuce varieties. Table 9 shows trial data comparing Icon and Pybas 251 iceberg lettuce varieties. Table 10 shows trial data comparing Pybas 251 and Icon iceberg lettuce varieties. Table 11 shows trial data comparing Spector and Icon iceberg lettuce Varieties. Table 12 shows trial data comparing Icon and Spector iceberg lettuce varieties. Table 13 shows trial data comparing Icon and Desert Spring iceberg lettuce varieties. Table 14 shows trial data comparing Icon and Desert Spring iceberg lettuce varieties. Table 15 shows trial data comparing Icon and Desert Spring iceberg lettuce varieties. Table 16 shows trial data comparing Icon and Spector iceberg lettuce varieties. Table 17 shows trial data comparing Icon and Spector iceberg lettuce varieties. Table 18 shows bolting data comparing Icon, Pybas 251 and Spector iceberg lettuce varieties.

TABLE 1

| Trial map #: | | Comparison of Head Characteristics | | Maturity Date: | |
| --- | --- | --- | --- | --- | --- |
| Wet Date: | 11/17/ | Location: | Dome Valley Ranch/lot: 30/4 | 1 Icon | 3/10/ |
| Date evald: | 3/10/ | Grower: | Nickerson Commercial Var Westland | 2 Spector | 3/8/ |

| | Core length (cm) | | Core diam. (cm) | | Head diam. (cm) | | Head length (cm) | |
| --- | --- | --- | --- | --- | --- | --- | --- | --- |
| Sample # | Icon | Spector | Icon | Spector | Icon | Spector | Icon | Spector |
| 1 | 5.1 | 3.3 | 4.3 | 3.6 | 16.8 | 14.0 | 14.3 | 14.2 |
| 2 | 4.3 | 3.4 | 3.9 | 4.1 | 15.3 | 14.9 | 12.9 | 14.0 |
| 3 | 4.6 | 2.7 | 4.0 | 3.1 | 16.2 | 13.9 | 15.7 | 13.3 |
| 4 | 4.7 | 4.4 | 3.5 | 3.8 | 15.1 | 16.5 | 13.7 | 15.2 |
| 5 | 3.6 | 4.0 | 3.5 | 3.9 | 14.3 | 14.7 | 14.2 | 13.4 |
| 6 | 3.4 | 4.5 | 3.5 | 4.2 | 16.4 | 14.2 | 15.3 | 14.7 |
| 7 | 3.9 | 3.2 | 3.8 | 4.0 | 16.2 | 14.1 | 13.8 | 13.9 |
| 8 | 3.8 | 3.7 | 3.7 | 3.8 | 16.2 | 14.8 | 14.1 | 14.4 |
| 9 | 3.5 | 3.9 | 4.5 | 4.0 | 19.0 | 15.7 | 13.7 | 14.0 |
| 10 | 3.0 | 3.6 | 3.5 | 3.9 | 15.9 | 14.6 | 15.1 | 13.5 |
| 11 | 4.0 | 4.0 | 3.7 | 3.8 | 16.4 | 16.4 | 16.3 | 14.3 |
| 12 | 5.4 | 3.0 | 4.0 | 4.2 | 15.4 | 14.3 | 14.6 | 13.5 |
| 13 | 5.0 | 4.2 | 3.9 | 3.0 | 16.9 | 14.3 | 15.0 | 14.4 |
| 14 | 4.0 | 2.5 | 3.9 | 3.5 | 16.2 | 14.4 | 15.6 | 13.2 |
| 15 | 3.1 | 3.7 | 4.0 | 3.8 | 16.9 | 14.4 | 14.8 | 13.4 |
| 16 | 3.5 | 2.7 | 4.4 | 4.1 | 17.0 | 15.5 | 13.0 | 12.9 |
| 17 | 5.1 | 3.5 | 3.7 | 4.5 | 16.9 | 14.6 | 15.6 | 14.1 |
| 18 | 5.6 | 3.4 | 4.5 | 4.1 | 15.1 | 15.2 | 14.0 | 13.6 |
| 19 | 5.1 | 3.3 | 4.0 | 4.0 | 15.7 | 15.5 | 15.3 | 13.5 |
| 20 | 4.2 | 3.2 | 3.4 | 3.6 | 15.6 | 14.7 | 15.6 | 14.9 |
| 21 | 4.0 | 4.0 | 3.8 | 4.5 | 16.4 | 15.7 | 14.3 | 14.0 |
| 22 | 3.5 | 3.1 | 3.9 | 4.1 | 15.8 | 14.5 | 14.5 | 13.9 |
| 23 | 4.8 | 2.4 | 3.8 | 3.8 | 16.7 | 16.0 | 14.2 | 13.3 |

TABLE 1-continued

| Trial map #: | | | Comparison of Head Characteristics | | | Maturity Date: | | |
|---|---|---|---|---|---|---|---|---|
| Wet Date: | 11/17/ | Location: | Dome Valley | Ranch/lot: 30/4 | | 1 Icon | 3/10/ | |
| Date evald: | 3/10/ | Grower: | Nickerson | Commercial Var Westland | | 2 Spector | 3/8/ | |

| | | | | | | | | |
|---|---|---|---|---|---|---|---|---|
| 24 | 3.0 | 2.5 | 3.8 | 3.6 | 15.9 | 13.0 | 15.0 | 13.2 |
| Average | 4.2 | 3.4 | 3.9 | 3.9 | 16.2 | 14.8 | 14.6 | 13.9 |
| Stan dev | 0.7788881 | 0.60235 | 0.309628 | 0.361458 | 0.911272 | 0.838984 | 0.872735 | 0.585823 |
| T test | 5.92E−04 | | 1.00E+00 | | 2.79E−06 | | 1.19E−03 | |

| | Avg Head Diameter (cm) | | Avg Head Diam: Core | | Frame diam (cm) | | Head wt. (g) | |
|---|---|---|---|---|---|---|---|---|
| Sample # | Icon | Spector | Icon | Spector | Icon | Spector | Icon | Spector |
| 1 | 15.6 | 14.1 | 3.0 | 4.3 | 44 | 49 | 840 | 934 |
| 2 | 14.1 | 14.5 | 3.3 | 4.3 | 43 | 48 | 851 | 747 |
| 3 | 16.0 | 13.6 | 3.5 | 5.0 | 54 | 46 | 867 | 599 |
| 4 | 14.4 | 15.9 | 3.1 | 3.6 | 48 | 51 | 939 | 996 |
| 5 | 14.3 | 14.1 | 4.0 | 3.2 | 43 | 50 | 771 | 635 |
| 6 | 15.9 | 14.5 | 4.7 | 3.6 | 46 | 48 | 1265 | 893 |
| 7 | 15.0 | 14.0 | 3.8 | 3.1 | 51 | 45 | 1107 | 837 |
| 8 | 15.2 | 14.6 | 4.0 | 4.6 | 49 | 54 | 946 | 1118 |
| 9 | 16.4 | 14.9 | 4.7 | 4.0 | 48 | 48 | 1114 | 852 |
| 10 | 15.5 | 14.1 | 5.2 | 3.6 | 47 | 49 | 1284 | 774 |
| 11 | 16.4 | 15.4 | 4.1 | 4.3 | 50 | 44 | 1225 | 600 |
| 12 | 15.0 | 13.9 | 2.8 | 3.5 | 49 | 49 | 1202 | 683 |
| 13 | 16.0 | 14.4 | 3.2 | 4.8 | 49 | 49 | 1350 | 879 |
| 14 | 15.9 | 13.8 | 4.0 | 3.3 | 51 | 47 | 769 | 777 |
| 15 | 15.9 | 13.9 | 5.1 | 5.6 | 49 | 46 | 905 | 654 |
| 16 | 15.0 | 14.2 | 4.3 | 3.8 | 47 | 48 | 948 | 780 |
| 17 | 16.3 | 14.4 | 3.2 | 4.1 | 48 | 50 | 1015 | 725 |
| 18 | 14.6 | 14.4 | 2.6 | 4.2 | 51 | 46 | 967 | 806 |
| 19 | 15.5 | 14.5 | 3.0 | 4.4 | 44 | 52 | 1022 | 902 |
| 20 | 15.6 | 14.8 | 3.7 | 4.6 | 50 | 55 | 980 | 769 |
| 21 | 15.4 | 14.9 | 3.8 | 3.7 | 54 | 49 | 1046 | 789 |
| 22 | 15.2 | 14.2 | 4.3 | 4.6 | 48 | 47 | 928 | 525 |
| 23 | 15.5 | 14.7 | 3.4 | 6.1 | 46 | 46 | 1204 | 809 |
| 24 | 15.5 | 13.1 | 5.2 | 5.2 | 51 | 50 | 940 | 810 |
| Average | 15.4 | 14.3 | 3.8 | 4.2 | 48.3 | 48.6 | 1020.2 | 787.2 |
| Stan dev | 0.6330246 | 0.566929 | 0.7547042 | 0.7553178 | 3.016860831 | 2.65259 | 164.6902 | 133.9257 |
| T test | 2.62E−07 | | 7.12E−02 | | 7.62E−01 | | 2.45E−06 | |

TABLE 2

| Trial map #: | | | Comparison of Head Characteristics | | | Maturity Date: | | |
|---|---|---|---|---|---|---|---|---|
| Wet Date: | 11/17/ | Location: | Dome Valley | Ranch/lot: 30/4 | | 1 Icon | 3/10/ | |
| Date evald: | 3/10/ | Grower: | Nickerson | Commercial Var Westland | | 2 Pybas251 | 3/8/ | |

| | Core length (cm) | | Core diam. (cm) | | Head diam. (cm) | | Head length (cm) | |
|---|---|---|---|---|---|---|---|---|
| Sample # | Icon | Pybas251 | Icon | Pybas251 | Icon | Pybas251 | Icon | Pybas251 |
| 1 | 5.1 | 6.2 | 4.3 | 3.7 | 16.8 | 15.0 | 14.3 | 16.2 |
| 2 | 4.3 | 4.2 | 3.9 | 4.0 | 15.3 | 15.1 | 12.9 | 16.4 |
| 3 | 4.6 | 4.7 | 4.0 | 3.8 | 16.2 | 15.7 | 15.7 | 16.5 |
| 4 | 4.7 | 3.7 | 3.5 | 3.5 | 15.1 | 15.2 | 13.7 | 15.1 |
| 5 | 3.6 | 3.7 | 3.5 | 3.7 | 14.3 | 15.3 | 14.2 | 15.5 |
| 6 | 3.4 | 5.5 | 3.5 | 4.2 | 16.4 | 17.1 | 15.3 | 17.4 |
| 7 | 3.9 | 4.2 | 3.8 | 4.1 | 16.2 | 15.1 | 13.8 | 15.7 |
| 8 | 3.8 | 3.7 | 3.7 | 3.5 | 16.2 | 14.5 | 14.1 | 15.5 |
| 9 | 3.5 | 3.1 | 4.5 | 4.0 | 19.0 | 15.7 | 13.7 | 15.8 |
| 10 | 3.0 | 4.2 | 3.5 | 4.0 | 15.9 | 15.7 | 15.1 | 16.1 |
| 11 | 4.0 | 6.0 | 3.7 | 3.4 | 16.4 | 16.8 | 16.3 | 15.8 |
| 12 | 5.4 | 3.6 | 4.0 | 3.9 | 15.4 | 15.5 | 14.6 | 14.7 |
| 13 | 5.0 | 4.0 | 3.9 | 3.7 | 16.9 | 15.2 | 15.0 | 17.1 |
| 14 | 4.0 | 5.2 | 3.9 | 3.5 | 16.2 | 14.7 | 15.6 | 17.2 |
| 15 | 3.1 | 2.9 | 4.0 | 4.0 | 16.9 | 16.9 | 14.8 | 15.4 |
| 16 | 3.5 | 3.0 | 4.4 | 3.7 | 17.0 | 16.7 | 13.0 | 15.3 |
| 17 | 5.1 | 4.2 | 3.7 | 3.7 | 16.9 | 17.9 | 15.6 | 17.0 |
| 18 | 5.6 | 4.2 | 4.5 | 3.7 | 15.1 | 17.1 | 14.0 | 17.3 |
| 19 | 5.1 | 4.5 | 4.0 | 3.8 | 15.7 | 15.6 | 15.3 | 16.1 |
| 20 | 4.2 | 4.2 | 3.4 | 3.6 | 15.6 | 17.0 | 15.6 | 14.7 |
| 21 | 4.0 | 2.2 | 3.8 | 3.9 | 16.4 | 13.0 | 14.3 | 13.3 |
| 22 | 3.5 | 5.4 | 3.9 | 3.3 | 15.8 | 17.3 | 14.5 | 15.5 |

TABLE 2-continued

| Trial map #: | | | Comparison of Head Characteristics | | | Maturity Date: | | |
|---|---|---|---|---|---|---|---|---|
| Wet Date: | 11/17/ | Location: | Dome Valley | Ranch/lot: 30/4 | | 1 Icon | 3/10/ | |
| Date evald: | 3/10/ | Grower: | Nickerson | Commercial Var Westland | | 2 Pybas251 | 3/8/ | |
| 23 | 4.6 | 4.7 | 3.8 | 3.9 | 16.7 | 15.5 | 14.2 | 16.5 |
| 24 | 3.0 | 4.5 | 3.8 | 3.6 | 15.9 | 17.5 | 15.0 | 15.7 |
| Average | 4.2 | 4.2 | 3.9 | 3.8 | 16.2 | 15.9 | 14.6 | 15.9 |
| Stan dev | 0.7788881 | 0.966804 | 0.309628 | 0.230154 | 0.911272 | 1.157576 | 0.872735 | 0.949129 |
| T test | 7.69E−01 | | 1.45E−01 | | 3.24E−01 | | 1.18E−05 | |

| | Avg Head Diameter (cm) | | Avg Head Diam: Core | | Frame diam (cm) | | Head wt. (g) | |
|---|---|---|---|---|---|---|---|---|
| Sample # | Icon | Pybas251 | Icon | Pybas251 | Icon | Pybas251 | Icon | Pybas251 |
| 1 | 15.6 | 15.6 | 3.0 | 2.5 | 44 | 45 | 840 | 1224 |
| 2 | 14.1 | 15.8 | 3.3 | 3.8 | 43 | 41 | 851 | 1288 |
| 3 | 16.0 | 16.1 | 3.5 | 3.4 | 54 | 40 | 867 | 977 |
| 4 | 14.4 | 15.2 | 3.1 | 4.1 | 48 | 52 | 939 | 1224 |
| 5 | 14.3 | 15.4 | 4.0 | 4.2 | 43 | 46 | 771 | 977 |
| 6 | 15.9 | 17.3 | 4.7 | 4.7 | 46 | 51 | 1265 | 1184 |
| 7 | 15.0 | 15.4 | 3.8 | 2.8 | 51 | 59 | 1107 | 744 |
| 8 | 15.2 | 15.0 | 4.0 | 3.6 | 49 | 49 | 946 | 1150 |
| 9 | 16.4 | 15.8 | 4.7 | 4.3 | 48 | 52 | 1114 | 1211 |
| 10 | 15.5 | 15.9 | 5.2 | 5.1 | 47 | 49 | 1284 | 1127 |
| 11 | 16.4 | 16.3 | 4.1 | 3.9 | 50 | 44 | 1225 | 986 |
| 12 | 15.0 | 15.1 | 2.8 | 2.5 | 49 | 45 | 1202 | 1013 |
| 13 | 16.0 | 16.2 | 3.2 | 4.5 | 49 | 45 | 1350 | 1167 |
| 14 | 15.9 | 16.0 | 4.0 | 4.0 | 51 | 50 | 769 | 1177 |
| 15 | 15.9 | 16.2 | 5.1 | 3.1 | 49 | 48 | 905 | 1320 |
| 16 | 15.0 | 16.0 | 4.3 | 5.5 | 47 | 47 | 948 | 1174 |
| 17 | 16.3 | 17.5 | 3.2 | 4.2 | 48 | 52 | 1015 | 1202 |
| 18 | 14.6 | 17.2 | 2.6 | 4.1 | 51 | 51 | 967 | 1517 |
| 19 | 15.5 | 15.9 | 3.0 | 3.5 | 44 | 45 | 1022 | 998 |
| 20 | 15.6 | 15.9 | 3.7 | 3.8 | 50 | 50 | 980 | 1013 |
| 21 | 15.4 | 13.2 | 3.8 | 6.0 | 54 | 48 | 1046 | 547 |
| 22 | 15.2 | 16.4 | 4.3 | 3.0 | 48 | 50 | 928 | 1200 |
| 23 | 15.5 | 16.0 | 3.4 | 3.4 | 46 | 45 | 1204 | 1118 |
| 24 | 15.5 | 16.6 | 5.2 | 3.7 | 51 | 47 | 940 | 878 |
| Average | 15.4 | 15.9 | 3.8 | 3.9 | 48.3 | 48.0 | 1020.2 | 1100.7 |
| Stan dev | 0.6330246 | 0.8651856 | 0.7547042 | 0.857926 | 3.016860831 | 4.069816 | 164.6902 | 197.6192 |
| T test | 2.70E−02 | | 7.60E−01 | | 7.19E−01 | | 1.32E−01 | |

TABLE 3

| Trial map #: | PD00003 | | Comparison of Head Characteristics | | | Maturity Date: | | |
|---|---|---|---|---|---|---|---|---|
| Wet Date: | 2/3/ | Location: | Spreckels | Ranch/Lot Spreckels/5 | | 1 Icon | 5/8/ | |
| Date evald: | 3/10/ | Grower: | C&M Cattle/T&A | Commercial variety: Mystic | | 2 Spector | 5/6/ | |

| | Core length (cm) | | Core diam. (cm) | | Head diam. (cm) | | Head length (cm) | |
|---|---|---|---|---|---|---|---|---|
| Sample # | Icon | Spector | Icon | Spector | Icon | Spector | Icon | Spector |
| 1 | 6.2 | 3.0 | 3.6 | 3.7 | 19.5 | 15.8 | 17.3 | 14.1 |
| 2 | 3.8 | 2.9 | 3.8 | 3.6 | 18.5 | 14.7 | 15.2 | 15.3 |
| 3 | 3.2 | 3.8 | 3.6 | 3.6 | 18.3 | 16.1 | 16.7 | 13.2 |
| 4 | 4.4 | 4.3 | 3.8 | 4.0 | 18.2 | 14.6 | 17.8 | 14.2 |
| 5 | 4.3 | 3.6 | 3.8 | 3.7 | 16.2 | 14.6 | 16.0 | 14.2 |
| 6 | 4.2 | 2.8 | 4.0 | 3.5 | 17.6 | 17.6 | 16.4 | 13.5 |
| 7 | 3.2 | 3.6 | 3.7 | 3.5 | 16.2 | 19.5 | 14.3 | 13.8 |
| 8 | 3.7 | 4.4 | 3.5 | 3.5 | 15.2 | 16.7 | 15.2 | 14.6 |
| 9 | 3.5 | 4.2 | 3.9 | 3.6 | 16.4 | 18.0 | 14.4 | 13.6 |
| 10 | 4.2 | 3.0 | 4.1 | 3.8 | 18.3 | 14.6 | 14.2 | 14.5 |
| 11 | 4.6 | 3.3 | 3.5 | 3.2 | 15.5 | 15.5 | 14.8 | 13.3 |
| 12 | 3.0 | 4.2 | 3.3 | 3.9 | 18.0 | 17.0 | 16.1 | 14.2 |
| 13 | 4.5 | 3.1 | 4.0 | 3.6 | 18.7 | 15.1 | 15.3 | 13.2 |
| 14 | 3.1 | 4.0 | 3.6 | 4.1 | 17.0 | 17.4 | 15.6 | 15.3 |
| 15 | 3.6 | 3.2 | 3.8 | 3.5 | 18.5 | 15.0 | 15.2 | 15.2 |
| 16 | 3.9 | 2.5 | 3.6 | 3.7 | 19.0 | 16.2 | 16.7 | 14.3 |
| 17 | 3.8 | 3.8 | 3.9 | 4.3 | 17.3 | 20.4 | 14.8 | 14.3 |
| 18 | 4.8 | 4.6 | 4.2 | 3.3 | 19.1 | 14.2 | 15.0 | 14.5 |
| 19 | 4.0 | 3.2 | 3.6 | 3.6 | 19.6 | 13.8 | 13.5 | 12.8 |
| 20 | 5.2 | 2.5 | 3.7 | 3.6 | 18.2 | 15.0 | 15.4 | 13.6 |
| 21 | 2.8 | 2.8 | 3.7 | 3.7 | 15.0 | 16.1 | 14.3 | 13.5 |

TABLE 3-continued

| Trial map #: | PD00003 | | Comparison of Head Characteristics | | | | Maturity Date: | |
|---|---|---|---|---|---|---|---|---|
| Wet Date: | 2/3/ | Location: | Spreckels | | Ranch/Lot Spreckels/5 | | 1 Icon | 5/8/ |
| Date evald: | 3/10/ | Grower: | C&M Cattle/T&A | | Commercial variety: Mystic | | 2 Spector | 5/6/ |

| | | | | | | | | |
|---|---|---|---|---|---|---|---|---|
| 22 | 4.3 | 3.5 | 4.4 | 3.2 | 17.3 | 17.0 | 15.3 | 15.3 |
| 23 | 3.5 | 3.0 | 4.0 | 4.1 | 15.1 | 17.7 | 14.9 | 16.2 |
| 24 | 3.0 | 3.6 | 3.8 | 3.3 | 17.0 | 15.4 | 16.2 | 16.3 |
| Average | 4.0 | 3.5 | 3.8 | 3.7 | 17.5 | 16.2 | 15.4 | 14.3 |
| Stan dev | 0.7874008 | 0.608619 | 0.247268 | 0.279751 | 1.408765 | 1.668289 | 1.042163 | 0.92872829 |
| T test | 0.0185636 | | 0.077757 | | 0.004805 | | 0.000206 | |

| | Avg Head Diameter (cm) | | Avg Head Diam: Core | | Frame diam (cm) | | Head wt. (g) | |
|---|---|---|---|---|---|---|---|---|
| Sample # | Icon | Spector | Icon | Spector | Icon | Spector | Icon | Spector |
| 1 | 18.4 | 15.0 | 3.0 | 5.0 | 52 | 50 | 1138 | 744 |
| 2 | 16.9 | 15.0 | 4.4 | 5.2 | 48 | 46 | 852 | 861 |
| 3 | 17.5 | 14.7 | 5.5 | 3.9 | 47 | 46 | 914 | 803 |
| 4 | 18.0 | 14.4 | 4.1 | 3.3 | 47 | 53 | 709 | 578 |
| 5 | 16.1 | 14.4 | 3.7 | 3.3 | 47 | 51 | 951 | 754 |
| 6 | 17.0 | 15.6 | 4.0 | 4.3 | 51 | 52 | 748 | 1102 |
| 7 | 15.3 | 16.7 | 4.8 | 5.9 | 49 | 51 | 904 | 931 |
| 8 | 15.2 | 15.7 | 4.1 | 4.3 | 51 | 50 | 939 | 981 |
| 9 | 15.4 | 15.8 | 4.4 | 3.6 | 48 | 51 | 768 | 865 |
| 10 | 16.3 | 14.6 | 3.9 | 3.5 | 48 | 54 | 885 | 474 |
| 11 | 15.2 | 14.4 | 3.3 | 4.8 | 50 | 51 | 1002 | 828 |
| 12 | 17.1 | 15.6 | 5.7 | 4.7 | 48 | 51 | 691 | 871 |
| 13 | 17.0 | 14.2 | 3.8 | 3.4 | 47 | 51 | 616 | 785 |
| 14 | 16.3 | 16.4 | 5.3 | 5.3 | 53 | 47 | 784 | 704 |
| 15 | 16.9 | 15.1 | 4.7 | 3.8 | 49 | 49 | 718 | 761 |
| 16 | 17.9 | 15.3 | 4.6 | 4.8 | 49 | 50 | 703 | 603 |
| 17 | 16.1 | 17.4 | 4.2 | 4.6 | 50 | 52 | 868 | 616 |
| 18 | 17.1 | 14.4 | 3.6 | 3.1 | 45 | 48 | 588 | 838 |
| 19 | 16.6 | 13.3 | 4.1 | 4.2 | 50 | 53 | 799 | 992 |
| 20 | 16.8 | 14.3 | 3.2 | 5.7 | 51 | 48 | 749 | 537 |
| 21 | 14.7 | 14.8 | 5.2 | 5.3 | 49 | 46 | 694 | 797 |
| 22 | 16.3 | 16.2 | 3.8 | 4.6 | 52 | 53 | 700 | 660 |
| 23 | 15.0 | 17.0 | 4.3 | 5.7 | 49 | 51 | 966 | 517 |
| 24 | 16.6 | 15.9 | 5.5 | 4.4 | 50 | 51 | 865 | 876 |
| Average | 16.5 | 15.2 | 4.3 | 4.4 | 49.2 | 50.2 | 814.6 | 769.9 |
| Stan dev | 0.9904058 | 0.9874117 | 0.7446001 | 0.8291634 | 1.926174 | 2.321528 | 132.71408 | 160.2411 |
| T test | 8.088E-05 | | 0.5303099 | | 0.097469 | | 0.2979831 | |

TABLE 4

| Trial map #: | PD00003 | | Comparison of Head Characteristics | | | | Maturity Date: | |
|---|---|---|---|---|---|---|---|---|
| Wet Date: | 2/3/ | Location: | Spreckels | | Ranch/Lot Spreckels/5 | | 1 Icon | 5/8/ |
| Date evald: | 3/10/ | Grower: | C&M Cattle/T&A | | Commercial variety: Mystic | | 2 Pybas 251 | 5/9/ |

| | Core length (cm) | | Core diam. (cm) | | Head diam. (cm) | | Head length (cm) | |
|---|---|---|---|---|---|---|---|---|
| Sample # | Icon | Pybas 251 | Icon | Pybas 251 | Icon | Pybas 251 | Icon | Pybas 251 |
| 1 | 6.2 | 5.0 | 3.6 | 3.6 | 19.5 | 17.2 | 17.3 | 16.2 |
| 2 | 3.8 | 4.2 | 3.8 | 3.3 | 18.5 | 17.5 | 15.2 | 16.4 |
| 3 | 3.2 | 4.3 | 3.6 | 3.4 | 18.3 | 14.8 | 16.7 | 15.6 |
| 4 | 4.4 | 4.4 | 3.6 | 3.2 | 18.2 | 16.1 | 17.8 | 15.3 |
| 5 | 4.3 | 2.8 | 3.8 | 3.5 | 16.2 | 15.1 | 16.0 | 15.5 |
| 6 | 4.2 | 4.6 | 4.0 | 3.6 | 17.6 | 16.2 | 16.4 | 16.0 |
| 7 | 3.2 | 4.1 | 3.7 | 3.7 | 16.2 | 17.5 | 14.3 | 17.4 |
| 8 | 3.7 | 3.2 | 3.5 | 3.1 | 15.2 | 17.3 | 15.2 | 15.1 |
| 9 | 3.5 | 3.3 | 3.9 | 3.3 | 16.4 | 16.0 | 14.4 | 17.3 |
| 10 | 4.2 | 3.1 | 4.1 | 3.3 | 18.3 | 16.5 | 14.2 | 14.8 |
| 11 | 4.6 | 6.2 | 3.5 | 3.5 | 15.5 | 18.5 | 14.8 | 15.3 |
| 12 | 3.0 | 5.7 | 3.3 | 3.8 | 18.0 | 16.2 | 16.1 | 16.0 |
| 13 | 4.5 | 4.0 | 3.6 | 3.2 | 18.7 | 17.2 | 15.3 | 17.3 |
| 14 | 3.1 | 4.6 | 3.6 | 4.1 | 17.0 | 18.5 | 15.6 | 18.0 |
| 15 | 3.6 | 2.1 | 3.8 | 3.3 | 18.5 | 15.2 | 15.2 | 14.8 |
| 16 | 3.9 | 4.0 | 3.6 | 3.7 | 19.0 | 16.2 | 16.7 | 15.6 |
| 17 | 3.8 | 5.0 | 3.9 | 3.5 | 17.3 | 17.2 | 14.8 | 16.3 |
| 18 | 4.8 | 2.8 | 4.2 | 3.1 | 19.1 | 14.5 | 15.0 | 13.3 |
| 19 | 4.0 | 3.8 | 3.6 | 3.2 | 19.6 | 14.5 | 13.5 | 15.7 |
| 20 | 5.2 | 3.0 | 3.7 | 3.0 | 18.2 | 15.2 | 15.4 | 14.3 |

TABLE 4-continued

| Trial map #: | PD00003 | | Comparison of Head Characteristics | | | | Maturity Date: | |
|---|---|---|---|---|---|---|---|---|
| Wet Date: | 2/3/ | Location: | Spreckels | | Ranch/Lot Spreckels/5 | | 1 Icon | 5/8/ |
| Date evald: | 3/10/ | Grower: | C&M Cattle/T&A | | Commercial variety: Mystic | | 2 Pybas 251 | 5/9/ |

| | | | | | | | | |
|---|---|---|---|---|---|---|---|---|
| 21 | 2.8 | 4.6 | 3.4 | 3.6 | 15.0 | 15.9 | 14.3 | 16.3 |
| 22 | 4.3 | 4.3 | 4.4 | 3.0 | 17.3 | 14.0 | 15.3 | 17.3 |
| 23 | 3.5 | 3.5 | 4.0 | 4.2 | 15.1 | 15.1 | 14.9 | 16.3 |
| 24 | 3.0 | 2.9 | 3.8 | 3.2 | 17.0 | 14.0 | 16.2 | 15.8 |
| Average | 4.0 | 4.0 | 3.8 | 3.4 | 17.5 | 16.1 | 15.4 | 15.9 |
| Stan dev | 0.7874008 | 0.980674 | 0.25876 | 0.315769 | 1.408765 | 1.318761 | 1.042163 | 1.080786 |
| T test | 0.9100391 | | 0.000423 | | 0.000978 | | 0.130651 | |

| | Avg Head Diameter (cm) | | Avg Head Diam: Core | | Frame diam (cm) | | Head wt. (g) | |
|---|---|---|---|---|---|---|---|---|
| Sample # | Icon | Pybas 251 | Icon | Pybas 251 | Icon | Pybas 251 | Icon | Pybas 251 |
| 1 | 18.4 | 16.7 | 3.0 | 3.3 | 42 | 49 | 1138 | 916 |
| 2 | 16.9 | 17.0 | 4.4 | 4.0 | 48 | 51 | 852 | 1112 |
| 3 | 17.5 | 15.2 | 5.5 | 3.5 | 47 | 50 | 914 | 692 |
| 4 | 18.0 | 15.7 | 4.1 | 3.6 | 47 | 53 | 709 | 700 |
| 5 | 16.1 | 15.3 | 3.7 | 3.5 | 47 | 52 | 951 | 634 |
| 6 | 17.0 | 16.1 | 4.0 | 5.8 | 51 | 51 | 748 | 960 |
| 7 | 15.3 | 17.5 | 4.8 | 3.8 | 49 | 50 | 904 | 781 |
| 8 | 15.2 | 16.2 | 4.1 | 4.0 | 51 | 52 | 939 | 611 |
| 9 | 15.4 | 16.7 | 4.4 | 5.2 | 48 | 50 | 768 | 995 |
| 10 | 16.3 | 15.7 | 3.9 | 4.7 | 48 | 51 | 885 | 576 |
| 11 | 15.2 | 16.9 | 3.3 | 5.5 | 50 | 52 | 1002 | 575 |
| 12 | 17.1 | 16.1 | 5.7 | 2.6 | 48 | 50 | 691 | 612 |
| 13 | 17.0 | 17.3 | 3.8 | 3.0 | 47 | 50 | 616 | 1375 |
| 14 | 16.3 | 18.3 | 5.3 | 4.6 | 53 | 48 | 784 | 994 |
| 15 | 16.9 | 15.0 | 4.7 | 3.3 | 49 | 51 | 718 | 716 |
| 16 | 17.9 | 15.9 | 4.6 | 7.6 | 49 | 50 | 703 | 701 |
| 17 | 16.1 | 16.8 | 4.2 | 3.4 | 50 | 49 | 868 | 1083 |
| 18 | 17.1 | 13.9 | 3.6 | 5.0 | 45 | 49 | 588 | 845 |
| 19 | 16.6 | 15.1 | 4.1 | 4.0 | 50 | 52 | 799 | 765 |
| 20 | 16.8 | 14.8 | 3.2 | 4.9 | 51 | 50 | 749 | 662 |
| 21 | 14.7 | 16.1 | 5.2 | 3.5 | 49 | 49 | 694 | 888 |
| 22 | 16.3 | 15.7 | 3.8 | 3.6 | 52 | 50 | 700 | 828 |
| 23 | 15.0 | 15.7 | 4.3 | 4.5 | 49 | 51 | 966 | 752 |
| 24 | 16.6 | 14.9 | 5.5 | 5.1 | 50 | 47 | 865 | 923 |
| Average | 16.5 | 16.0 | 4.3 | 4.2 | 49.2 | 50.3 | 814.6 | 820.7 |
| Stan dev | 0.9904058 | 0.9899838 | 0.7446001 | 1.0943999 | 1.926174 | 1.398109 | 132.71408 | 197.71338 |
| T test | 0.1160064 | | 0.839992 | | 0.025092 | | 0.9016225 | |

TABLE 5

| Trial map #: | RSV99084 | | Comparison of Head Characteristics | | | | | |
|---|---|---|---|---|---|---|---|---|
| Wet Date: | 8/6/ | Location: | Blanco | | Ranch/lot: Bardin 14 | | | |
| Date vald: | 3/10/ | Grower: | RC Farms | | Commerci Venus | | | |

| | Core length (cm) | | Core diam. (cm) | | Head diam. (cm) | | Head length (cm) | |
|---|---|---|---|---|---|---|---|---|
| Sample # | Icon | Spector | Icon | Spector | Icon | Spector | Icon | Spector |
| 1 | 4.9 | 3.6 | 3.8 | 3.8 | 17.8 | 14.4 | 16.5 | 14.5 |
| 2 | 5.2 | 3.1 | 3.9 | 3.7 | 16.0 | 13.2 | 12.8 | 13.1 |
| 3 | 4.6 | 4.5 | 3.5 | 3.5 | 16.6 | 13.6 | 15.1 | 14.1 |
| 4 | 2.5 | 3.2 | 4.0 | 3.7 | 16.4 | 15.4 | 15.1 | 13.5 |
| 5 | 6.4 | 4.3 | 4.1 | 3.0 | 18.6 | 14.5 | 14.9 | 15.3 |
| 6 | 5.1 | 5.2 | 3.6 | 3.1 | 15.2 | 14.6 | 18.5 | 14.9 |
| 7 | 5.1 | 4.4 | 3.8 | 3.2 | 18.1 | 15.7 | 14.3 | 12.4 |
| 8 | 6.2 | 6.2 | 3.5 | 3.6 | 18.1 | 16.2 | 15.1 | 16.6 |
| 9 | 4.3 | 4.6 | 3.2 | 3.5 | 15.2 | 14.5 | 13.1 | 13.9 |
| 10 | 5.6 | 4.8 | 3.5 | 3.1 | 16.4 | 14.5 | 16.0 | 14.9 |
| 11 | 5.2 | 5.2 | 3.6 | 3.6 | 15.2 | 15.1 | 13.1 | 13.9 |
| 12 | 5.1 | 4.2 | 3.6 | 3.4 | 16.2 | 15.4 | 14.0 | 13.5 |
| 13 | 3.2 | 5.0 | 3.7 | 3.0 | 15.7 | 15.6 | 13.2 | 13.6 |
| 14 | 3.9 | 4.0 | 4.2 | 3.0 | 16.9 | 15.5 | 15.4 | 13.6 |
| 15 | 3.7 | 4.0 | 3.5 | 3.2 | 17.9 | 15.9 | 17.5 | 14.2 |
| 16 | 7.4 | 3.7 | 3.6 | 3.1 | 17.9 | 16.0 | 14.8 | 14.2 |
| 17 | 4.6 | 5.9 | 3.0 | 3.5 | 14.5 | 15.2 | 14.5 | 13.1 |
| 18 | 5.4 | 3.1 | 3.6 | 3.2 | 16.0 | 14.4 | 14.9 | 12.1 |
| 19 | 6.6 | 3.1 | 3.7 | 3.2 | 17.9 | 14.5 | 17.9 | 14.1 |

TABLE 5-continued

Trial map #: RSV99084     Comparison of Head Characteristics

Wet Date: 8/6/     Location: Blanco     Ranch/lot: Bardin 14
Date vald: 3/10/     Grower: RC Farms     Commerci Venus

| | | | | | | | | |
|---|---|---|---|---|---|---|---|---|
| 20 | 5.0 | 3.2 | 3.5 | 3.2 | 18.6 | 13.5 | 16.4 | 14.6 |
| 21 | 5.5 | 4.4 | 3.2 | 3.1 | 15.5 | 15.1 | 16.1 | 13.2 |
| 22 | 6.1 | 5.5 | 3.5 | 3.3 | 17.4 | 14.5 | 15.5 | 12.8 |
| 23 | 8.6 | 4.6 | 3.6 | 3.4 | 14.6 | 14.4 | 16.5 | 14.0 |
| 24 | 3.0 | 3.0 | 3.5 | 3.4 | 16.5 | 16.4 | 15.6 | 14.2 |
| Average | 5.1 | 4.3 | 3.6 | 3.3 | 16.6 | 14.9 | 15.3 | 13.9 |
| Stan dev | 1.3760898 | 0.924858 | 0.272369 | 0.243614 | 1.268229 | 0.846465 | 1.497147 | 0.964806 |
| T test | 1.56E−02 | | 3.58E−04 | | 1.60E−06 | | 5.33E−04 | |

| | Avg Head Diameter (cm | | Avg Head Diam: Core | | Frame diam (cm) | | Head wt. (g) | |
|---|---|---|---|---|---|---|---|---|
| Sample # | Icon | Spector | Icon | Spector | Icon | Spector | Icon | Spector |
| 1 | 17.2 | 14.5 | 3.5 | 4.0 | 52 | 50 | 826 | 554 |
| 2 | 14.4 | 13.2 | 2.8 | 4.2 | 53 | 52 | 890 | 566 |
| 3 | 15.9 | 13.9 | 3.4 | 3.1 | 52 | 50 | 644 | 690 |
| 4 | 15.8 | 14.5 | 6.3 | 4.5 | 50 | 48 | 714 | 814 |
| 5 | 16.8 | 14.9 | 2.6 | 4.7 | 53 | 47 | 838 | 578 |
| 6 | 16.9 | 14.8 | 3.3 | 3.4 | 51 | 46 | 722 | 550 |
| 7 | 16.2 | 14.1 | 3.2 | 2.7 | 49 | 51 | 874 | 572 |
| 8 | 16.6 | 16.4 | 2.7 | 3.7 | 49 | 46 | 532 | 698 |
| 9 | 14.2 | 14.2 | 3.3 | 2.3 | 51 | 48 | 994 | 515 |
| 10 | 16.2 | 14.7 | 2.9 | 3.2 | 52 | 46 | 714 | 630 |
| 11 | 14.2 | 14.5 | 2.7 | 3.0 | 53 | 50 | 694 | 698 |
| 12 | 15.1 | 14.5 | 3.0 | 2.8 | 51 | 47 | 690 | 422 |
| 13 | 14.5 | 14.6 | 4.5 | 3.5 | 53 | 51 | 602 | 706 |
| 14 | 16.2 | 14.6 | 4.1 | 2.9 | 51 | 44 | 608 | 480 |
| 15 | 17.7 | 15.1 | 4.8 | 3.8 | 52 | 49 | 746 | 708 |
| 16 | 16.4 | 15.1 | 2.2 | 3.8 | 51 | 46 | 874 | 646 |
| 17 | 14.5 | 14.2 | 3.2 | 2.4 | 51 | 49 | 770 | 470 |
| 18 | 15.5 | 13.3 | 2.9 | 4.3 | 51 | 49 | 700 | 606 |
| 19 | 17.9 | 14.3 | 2.7 | 4.6 | 55 | 48 | 800 | 520 |
| 20 | 17.5 | 14.1 | 3.5 | 4.4 | 54 | 50 | 944 | 876 |
| 21 | 15.8 | 14.2 | 2.9 | 3.2 | 53 | 47 | 722 | 846 |
| 22 | 16.5 | 13.7 | 2.7 | 2.5 | 52 | 49 | 774 | 516 |
| 23 | 15.6 | 14.2 | 1.8 | 3.1 | 51 | 49 | 772 | 580 |
| 24 | 16.1 | 15.3 | 5.4 | 5.1 | 50 | 48 | 760 | 614 |
| Average | 16.0 | 14.4 | 3.3 | 3.5 | 51.7 | 48.3 | 758.5 | 619.0 |
| Stan dev | 1.0955113 | 0.6743757 | 1.0200609 | 0.7937992 | 1.4645571 | 1.948615 | 109.8636 | 117.6626 |
| T test | 5.04E−07 | | 4.45E−01 | | 2.58E−08 | | 1.04E−04 | |

TABLE 6

Trial map #: RSV99084     Comparison of Head Characteristics

Wet Date: 8/6/     Location: Blanco     Ranch/lot: Bardin 14
Date vald: 3/10/     Grower: RC Farms     Commerci Venus

| | Core length (cm) | | Core diam. (cm) | | Head diam. (cm) | | Head length (cm) | |
|---|---|---|---|---|---|---|---|---|
| Sample # | Icon | Pybas 251 | Icon | Pybas 251 | Icon | Pybas 251 | Icon | Pybas 251 |
| 1 | 4.9 | 3.6 | 3.8 | 3.5 | 17.8 | 16.2 | 16.5 | 19.3 |
| 2 | 5.2 | 4.9 | 3.9 | 3.5 | 16.0 | 18.1 | 12.8 | 14.9 |
| 3 | 4.6 | 5.5 | 3.5 | 3.9 | 16.6 | 17.2 | 15.1 | 17.9 |
| 4 | 2.5 | 4.9 | 4.0 | 3.5 | 16.4 | 17.1 | 15.1 | 17.6 |
| 5 | 6.4 | 4.4 | 4.1 | 3.0 | 18.6 | 17.4 | 14.9 | 17.5 |
| 6 | 5.1 | 3.6 | 3.6 | 3.2 | 15.2 | 15.0 | 18.5 | 14.6 |
| 7 | 5.1 | 4.6 | 3.8 | 3.5 | 18.1 | 18.1 | 14.3 | 17.2 |
| 8 | 6.2 | 5.2 | 3.5 | 3.9 | 18.1 | 16.5 | 15.1 | 14.4 |
| 9 | 4.3 | 5.6 | 3.2 | 3.2 | 15.2 | 17.9 | 13.1 | 15.9 |
| 10 | 5.6 | 3.9 | 3.5 | 3.7 | 16.4 | 16.5 | 16.0 | 16.4 |
| 11 | 5.2 | 5.5 | 3.6 | 3.6 | 15.5 | 16.4 | 13.1 | 16.2 |
| 12 | 5.1 | 3.9 | 3.6 | 3.5 | 16.2 | 15.9 | 14.0 | 18.1 |
| 13 | 3.2 | 3.6 | 3.7 | 3.5 | 15.7 | 15.6 | 13.2 | 16.1 |
| 14 | 3.9 | 4.0 | 4.2 | 3.4 | 16.9 | 16.2 | 15.4 | 16.1 |
| 15 | 3.7 | 4.4 | 3.5 | 3.2 | 17.9 | 15.9 | 17.5 | 16.5 |
| 16 | 7.4 | 5.1 | 3.6 | 3.6 | 17.9 | 15.5 | 14.8 | 18.1 |
| 17 | 4.6 | 4.5 | 3.0 | 3.2 | 14.5 | 18.5 | 14.5 | 15.5 |
| 18 | 5.4 | 6.2 | 3.6 | 3.0 | 16.0 | 16.9 | 14.9 | 17.4 |

TABLE 6-continued

Trial map #: RSV99084 — Comparison of Head Characteristics

Wet Date: 8/6/   Location: Blanco   Ranch/lot: Bardin 14
Date vald: 3/10/   Grower: RC Farms   Commerci Venus

| Sample # | | | | | | | | |
|---|---|---|---|---|---|---|---|---|
| 19 | 6.6 | 3.2 | 3.7 | 3.5 | 17.9 | 16.4 | 17.9 | 15.7 |
| 20 | 5.0 | 4.0 | 3.5 | 3.2 | 18.6 | 17.2 | 16.4 | 16.1 |
| 21 | 5.5 | 3.5 | 3.2 | 3.6 | 15.5 | 16.2 | 16.1 | 16.0 |
| 22 | 6.1 | 4.9 | 3.5 | 3.3 | 17.4 | 16.6 | 15.5 | 16.5 |
| 23 | 8.6 | 5.6 | 3.6 | 3.8 | 14.6 | 17.7 | 16.5 | 16.6 |
| 24 | 3.0 | 3.6 | 3.5 | 3.4 | 16.5 | 16.6 | 15.6 | 16.4 |
| Average | 5.1 | 4.5 | 3.6 | 3.4 | 16.6 | 16.7 | 15.3 | 16.5 |
| Stan dev | 1.3760898 | 0.829309 | 0.272369 | 0.248437 | 1.254896 | 0.899597 | 1.497147 | 1.176183 |
| T test | 6.29E−02 | | 3.18E−02 | | 7.83E−01 | | 2.24E−03 | |

| | Avg Head Diameter (cm) | | Avg Head Diam: Core | | Frame diam (cm) | | Head wt. (g) | |
|---|---|---|---|---|---|---|---|---|
| Sample # | Icon | Pybas 251 | Icon | Pybas 251 | Icon | Pybas 251 | Icon | Pybas 251 |
| 1 | 17.2 | 17.8 | 3.5 | 4.9 | 52 | 525349 | 826 | 736 |
| 2 | 14.4 | 16.5 | 2.8 | 3.4 | 53 | 51 | 890 | 710 |
| 3 | 15.9 | 17.6 | 3.4 | 3.2 | 52 | 50 | 644 | 842 |
| 4 | 15.8 | 17.4 | 6.3 | 3.5 | 50 | 52 | 714 | 600 |
| 5 | 16.8 | 17.5 | 2.6 | 3.6 | 53 | 50 | 838 | 624 |
| 6 | 16.9 | 14.8 | 3.3 | 3.4 | 51 | 54 | 722 | 702 |
| 7 | 16.2 | 17.7 | 3.2 | 4.9 | 49 | 55 | 874 | 724 |
| 8 | 16.6 | 15.5 | 2.7 | 3.4 | 49 | 50 | 532 | 696 |
| 9 | 14.2 | 16.9 | 3.3 | 3.3 | 51 | 51 | 994 | 732 |
| 10 | 16.2 | 16.5 | 2.9 | 2.9 | 52 | 52 | 714 | 652 |
| 11 | 14.3 | 16.3 | 2.8 | 4.2 | 53 | 50 | 694 | 630 |
| 12 | 15.1 | 17.0 | 3.0 | 3.1 | 51 | 51 | 690 | 816 |
| 13 | 14.5 | 15.9 | 4.5 | 4.1 | 53 | 50 | 602 | 930 |
| 14 | 16.2 | 16.2 | 4.1 | 4.5 | 51 | 53 | 608 | 830 |
| 15 | 17.7 | 16.2 | 4.8 | 4.1 | 52 | 51 | 746 | 868 |
| 16 | 16.4 | 16.8 | 2.2 | 3.8 | 51 | 47 | 874 | 652 |
| 17 | 14.5 | 17.0 | 3.2 | 3.8 | 51 | 53 | 770 | 638 |
| 18 | 15.5 | 17.2 | 2.9 | 2.8 | 51 | 50 | 700 | 642 |
| 19 | 17.9 | 16.1 | 2.7 | 5.0 | 55 | 52 | 800 | 644 |
| 20 | 17.5 | 16.7 | 3.5 | 4.2 | 54 | 49 | 944 | 928 |
| 21 | 15.8 | 16.1 | 2.9 | 4.6 | 53 | 51 | 722 | 746 |
| 22 | 16.5 | 16.6 | 2.7 | 3.4 | 52 | 50 | 774 | 1202 |
| 23 | 15.6 | 17.2 | 1.8 | 3.1 | 51 | 53 | 772 | 844 |
| 24 | 16.1 | 16.5 | 5.4 | 4.6 | 50 | 51 | 760 | 774 |
| Average | 16.0 | 16.6 | 3.3 | 3.8 | 51.7 | 54.0 | 758.5 | 756.8 |
| Stan dev | 1.0851246 | 0.7166119 | 1.0193117 | 0.6760024 | 1.4645571 | 107226 | 109.8636 | 135.98441 |
| T test | 1.47E−02 | | 6.92E−02 | | 3.23E−01 | | 9.61E−01 | |

TABLE 7

Trial map #: SV00119   Comparison of Head Characteristics   Maturity Date:

Wet Date: 4/11/   Location: Salinas   Ranch/lot: Cooper/5   1 Spector 6/21/
Date evald: 6/20/   Grower: Blanco   Commercial Var Sharpshoote   2 Icon 6/24/

| | Core length (cm) | | Core diam. (cm) | | Head diam. (cm) | | Head length (cm) | |
|---|---|---|---|---|---|---|---|---|
| Sample # | Icon | Spector | Icon | Spector | Icon | Spector | Icon | Spector |
| 1 | 3.5 | 4.7 | 3.5 | 4.0 | 14.6 | 14.5 | 13.6 | 16.1 |
| 2 | 4.1 | 4.2 | 3.6 | 3.8 | 13.1 | 15.5 | 14.2 | 16.4 |
| 3 | 3.3 | 4.6 | 4.2 | 3.4 | 16.0 | 15.0 | 15.4 | 13.2 |
| 4 | 3.7 | 2.5 | 3.5 | 3.1 | 14.4 | 16.0 | 13.7 | 13.5 |
| 5 | 3.0 | 2.3 | 4.0 | 3.5 | 13.7 | 14.9 | 13.7 | 14.2 |
| 6 | 4.1 | 2.5 | 3.9 | 3.7 | 14.3 | 11.5 | 13.5 | 16.6 |
| 7 | 2.5 | 3.5 | 4.0 | 3.7 | 14.3 | 14.6 | 14.5 | 13.8 |
| 8 | 3.0 | 2.9 | 3.8 | 3.6 | 17.0 | 13.7 | 14.5 | 14.5 |
| 9 | 3.0 | 4.0 | 3.9 | 3.2 | 12.9 | 16.5 | 14.7 | 12.2 |
| 10 | 2.9 | 4.1 | 3.9 | 3.3 | 13.7 | 13.0 | 15.3 | 15.2 |
| 11 | 3.0 | 2.6 | 3.7 | 3.5 | 13.0 | 14.9 | 13.6 | 14.6 |
| 12 | 3.1 | 4.7 | 3.7 | 3.9 | 14.5 | 14.9 | 13.5 | 15.9 |
| 13 | 4.0 | 4.0 | 3.2 | 3.6 | 14.0 | 16.0 | 15.2 | 15.0 |
| 14 | 4.4 | 4.0 | 3.5 | 3.6 | 13.4 | 14.0 | 15.2 | 14.7 |
| 15 | 2.5 | 4.0 | 3.8 | 3.6 | 13.8 | 16.4 | 13.1 | 16.0 |
| 16 | 3.0 | 3.7 | 3.6 | 3.5 | 14.0 | 15.1 | 14.9 | 14.3 |
| 17 | 3.1 | 4.2 | 3.7 | 4.0 | 13.0 | 15.0 | 15.5 | 15.4 |

TABLE 7-continued

| Trial map #: | SV00119 | | Comparison of Head Characteristics | | | | Maturity Date: | |
|---|---|---|---|---|---|---|---|---|
| Wet Date: | 4/11/ | Location: | Salinas | Ranch/lot: Cooper/5 | | | 1 Spector | 6/21/ |
| Date evald: | 6/20/ | Grower: | Blanco | Commercial Var Sharpshoote | | | 2 Icon | 6/24/ |
| 18 | 4.0 | 3.5 | 3.7 | 3.7 | 13.4 | 14.5 | 13.4 | 16.5 |
| 19 | 2.5 | 3.0 | 3.0 | 3.9 | 15.1 | 13.0 | 13.7 | 14.1 |
| 20 | 3.5 | 3.5 | 3.7 | 3.4 | 12.2 | 16.0 | 15.3 | 14.4 |
| 21 | 3.5 | 4.3 | 3.3 | 3.7 | 14.6 | 16.0 | 14.0 | 14.7 |
| 22 | 3.5 | 3.6 | 3.7 | 3.4 | 14.0 | 14.0 | 15.7 | 15.1 |
| 23 | 3.4 | 4.5 | 3.7 | 3.6 | 13.5 | 15.3 | 13.9 | 14.5 |
| 24 | 3.0 | 3.9 | 3.4 | 3.7 | 13.2 | 15.5 | 14.0 | 16.0 |
| Average | 3.3 | 3.7 | 3.7 | 3.6 | 14.0 | 14.8 | 14.3 | 14.9 |
| Stan dev | 0.5313368 | 0.727712 | 0.269729 | 0.232192 | 1.034329 | 1.166812 | 0.8004415 | 1.113349 |
| T test | 4.27E−02 | | 3.64E−01 | | 1.60E−02 | | 6.30E−02 | |

| | Avg Head Diameter (cm | | Avg Head Diam: Core | | Frame diam (cm) | | Head wt. (g) |
|---|---|---|---|---|---|---|---|
| Sample # | Spector | Icon | Spector | Icon | Spector | Icon | Spector |
| 1 | 14.1 | 15.3 | 4.0 | 3.3 | 42 | 43 | 1026 |
| 2 | 13.7 | 16.0 | 3.3 | 3.8 | 39 | 41 | 1152 |
| 3 | 15.7 | 14.1 | 4.8 | 3.1 | 40 | 44 | 930 |
| 4 | 14.1 | 14.8 | 3.8 | 5.9 | 41 | 44 | 982 |
| 5 | 13.7 | 14.6 | 4.6 | 5.8 | 42 | 40 | 864 |
| 6 | 13.9 | 14.1 | 3.4 | 6.1 | 43 | 38 | 940 |
| 7 | 14.4 | 14.2 | 5.8 | 5.7 | 43 | 48 | 740 |
| 8 | 15.8 | 14.1 | 5.3 | 4.0 | 46 | 44 | 931 |
| 9 | 13.8 | 14.4 | 4.6 | 4.9 | 43 | 46 | 858 |
| 10 | 14.5 | 14.1 | 5.0 | 3.5 | 43 | 45 | 903 |
| 11 | 13.3 | 14.8 | 4.4 | 3.6 | 46 | 48 | 1058 |
| 12 | 14.0 | 15.4 | 4.5 | 5.9 | 43 | 44 | 1111 |
| 13 | 14.6 | 15.5 | 3.7 | 3.3 | 48 | 45 | 912 |
| 14 | 14.3 | 14.4 | 3.3 | 3.6 | 46 | 47 | 978 |
| 15 | 13.5 | 16.2 | 5.4 | 4.1 | 40 | 44 | 910 |
| 16 | 14.5 | 14.7 | 4.8 | 3.7 | 46 | 43 | 1007 |
| 17 | 14.3 | 15.2 | 4.6 | 3.6 | 46 | 45 | 931 |
| 18 | 13.4 | 15.5 | 3.4 | 4.4 | 43 | 43 | 1059 |
| 19 | 14.4 | 13.6 | 5.8 | 4.5 | 43 | 45 | 1042 |
| 20 | 13.8 | 15.2 | 3.9 | 4.3 | 44 | 44 | 923 |
| 21 | 14.3 | 14.9 | 4.1 | 3.5 | 46 | 44 | 995 |
| 22 | 14.9 | 14.6 | 4.2 | 4.0 | 43 | 46 | 1042 |
| 23 | 13.7 | 14.9 | 4.0 | 3.3 | 44 | 47 | 854 |
| 24 | 13.6 | 15.8 | 4.5 | 4.0 | 46 | 42 | 1033 |
| Average | 14.2 | 14.8 | 4.4 | 4.3 | 43.6 | 44.2 | 965.9 |
| Stan dev | 0.6309499 | 0.6785501 | 0.7315197 | 0.9646309 | 2.301543276 | 2.3713263 | 92.6134146 |
| T test | 1.00E−03 | | 6.11E−01 | | 3.92E−01 | | 1.35E−06 |

TABLE 8

| Trial map #: | SV00119 | | Comparison of Head Characteristics | | | | Maturity Date: | |
|---|---|---|---|---|---|---|---|---|
| Wet Date: | 4/11/ | Location: | Salinas | Ranch/lot: Cooper/5 | | | 1 Pybas 251 | 6/24/ |
| Date evald: | 6/20/ | Grower: | Blanco | Commercial Var Sharpshoote | | | 2 Icon | 6/24/ |
| | Core length (cm) | | Core diam. (cm) | | Head diam. (cm) | | Head length (cm) | |
| Sample # | Pybas 251 | Icon | Pybas 251 | Icon | Pybas 251 | Icon | Pybas 251 | Icon |
| 1 | 4.6 | 4.7 | 3.1 | 4.0 | 17.1 | 14.5 | 16.2 | 16.1 |
| 2 | 3.9 | 4.2 | 3.5 | 3.8 | 16.5 | 15.5 | 15.7 | 16.4 |
| 3 | 3.0 | 4.6 | 3.3 | 3.4 | 15.4 | 15.0 | 14.3 | 13.2 |
| 4 | 3.0 | 2.5 | 3.6 | 3.1 | 12.6 | 16.0 | 15.7 | 13.5 |
| 5 | 2.7 | 2.3 | 3.4 | 3.5 | 17.0 | 14.9 | 14.9 | 14.2 |
| 6 | 2.6 | 2.5 | 3.4 | 3.7 | 15.5 | 11.5 | 16.3 | 16.6 |
| 7 | 3.5 | 3.5 | 3.8 | 3.7 | 17.6 | 14.6 | 15.5 | 13.8 |
| 8 | 5.0 | 2.9 | 4.0 | 3.6 | 17.5 | 13.7 | 16.5 | 14.5 |
| 9 | 4.5 | 4.0 | 3.4 | 3.2 | 17.0 | 16.5 | 15.0 | 12.2 |
| 10 | 3.8 | 4.1 | 3.6 | 3.3 | 16.3 | 13.0 | 15.6 | 15.2 |
| 11 | 4.0 | 2.6 | 3.6 | 3.5 | 17.0 | 14.9 | 17.4 | 14.6 |
| 12 | 3.5 | 4.7 | 3.7 | 3.9 | 15.3 | 14.9 | 15.5 | 15.9 |
| 13 | 4.0 | 4.0 | 3.2 | 3.6 | 16.5 | 16.0 | 17.3 | 15.0 |
| 14 | 4.0 | 4.0 | 4.0 | 3.6 | 16.5 | 14.0 | 15.0 | 14.7 |
| 15 | 3.5 | 4.0 | 3.5 | 3.6 | 16.3 | 16.4 | 15.7 | 16.0 |
| 16 | 3.5 | 3.7 | 4.0 | 3.5 | 17.1 | 15.1 | 15.7 | 14.3 |

TABLE 8-continued

| Trial map #: | SV00119 | | Comparison of Head Characteristics | | | | Maturity Date: | |
|---|---|---|---|---|---|---|---|---|
| Wet Date: | 4/11/ | Location: | Salinas | Ranch/lot: Cooper/5 | | | 1 Pybas 251 | 6/24/ |
| Date evald: | 6/20/ | Grower: | Blanco | Commercial Var Sharpshoote | | | 2 Icon | 6/24/ |
| 17 | 3.0 | 4.2 | 3.5 | 4.0 | 15.3 | 15.0 | 16.1 | 15.4 |
| 18 | 3.7 | 3.5 | 3.4 | 3.7 | 17.1 | 14.5 | 14.8 | 16.5 |
| 19 | 2.9 | 3.0 | 3.6 | 3.9 | 17.6 | 13.0 | 15.4 | 14.1 |
| 20 | 3.3 | 3.5 | 3.4 | 3.4 | 16.3 | 16.0 | 15.5 | 14.4 |
| 21 | 3.1 | 4.3 | 3.5 | 3.7 | 16.8 | 15.0 | 14.0 | 14.7 |
| 22 | | 3.6 | 3.5 | 3.4 | | 14.0 | | 15.1 |
| 23 | | 4.5 | 3.8 | 3.6 | | 15.3 | | 14.5 |
| 24 | | 3.9 | 3.5 | 3.7 | | 15.5 | | 16.0 |
| Average | 3.6 | 3.7 | 3.3 | 3.6 | 16.4 | 14.8 | 15.6 | 14.9 |
| Stan Dev | 0.6378909 | 0.727712 | 0.235869 | 0.232192 | 1.129812 | 1.166812 | 0.843744 | 1.113349 |
| T test | 5.50E−01 | | 5.01E−01 | | 2.76E−05 | | 1.52E−02 | |

| | Avg Head Diameter (cm | | Avg Head Diam: Core | | Frame diam (cm) | | Head wt. (g) | |
|---|---|---|---|---|---|---|---|---|
| Sample # | Pybas 251 | Icon | Pybas 251 | Icon | Pybas 251 | Icon | Pybas 251 | Icon |
| 1 | 16.7 | 15.3 | 3.6 | 3.3 | 45 | 43 | 564 | 869 |
| 2 | 16.1 | 16.0 | 4.1 | 3.8 | 45 | 41 | 1046 | 1011 |
| 3 | 14.9 | 14.1 | 5.0 | 3.1 | 48 | 44 | 1058 | 531 |
| 4 | 14.2 | 14.8 | 4.7 | 5.9 | 41 | 44 | 769 | 838 |
| 5 | 16.0 | 14.6 | 5.9 | 5.8 | 40 | 40 | 772 | 933 |
| 6 | 15.9 | 14.1 | 6.1 | 6.1 | 41 | 38 | 840 | 889 |
| 7 | 16.6 | 14.2 | 4.7 | 5.7 | 44 | 48 | 755 | 962 |
| 8 | 17.0 | 14.1 | 3.4 | 4.0 | 46 | 44 | 810 | 955 |
| 9 | 16.0 | 14.4 | 3.6 | 4.9 | 47 | 46 | 705 | 833 |
| 10 | 16.0 | 14.1 | 4.2 | 3.5 | 40 | 45 | 709 | 799 |
| 11 | 17.2 | 14.8 | 4.3 | 3.6 | 50 | 48 | 1008 | 975 |
| 12 | 15.4 | 15.4 | 4.4 | 5.9 | 45 | 44 | 758 | 752 |
| 13 | 16.9 | 15.5 | 4.2 | 3.3 | 45 | 45 | 687 | 1044 |
| 14 | 15.8 | 14.4 | 3.9 | 3.6 | 46 | 47 | 987 | 784 |
| 15 | 16.0 | 16.2 | 4.6 | 4.1 | 44 | 44 | 944 | 768 |
| 16 | 16.4 | 14.7 | 4.7 | 37 | 41 | 43 | 647 | 726 |
| 17 | 15.7 | 15.2 | 5.2 | 3.6 | 49 | 45 | 1015 | 909 |
| 18 | 16.0 | 15.5 | 4.3 | 4.4 | 43 | 43 | 1076 | 852 |
| 19 | 16.5 | 13.6 | 5.7 | 4.5 | 42 | 45 | 875 | 764 |
| 20 | 15.9 | 15.2 | 4.8 | 4.3 | 43 | 44 | 671 | 740 |
| 21 | 15.4 | 14.9 | 5.0 | 3.5 | 47 | 44 | 1051 | 645 |
| 22 | | 14.6 | | 4.0 | | 46 | | 764 |
| 23 | | 14.9 | | 3.3 | | 47 | | 791 |
| 24 | | 15.8 | | 4.0 | | 42 | | 983 |
| Average | 16.0 | 14.8 | 4.6 | 4.3 | 44.4 | 44.2 | 845.1 | 838.2 |
| Stan dev | 0.7084524 | 0.6785501 | 0.7282454 | 0.9646309 | 2.906478806 | 2.371326 | 159.28368 | 122.0499 |
| T test | 9.53E−07 | | 1.91E—01 | | 7.87E−01 | | 8.71E−01 | |

TABLE 9

| Trial map #: | SVPD99003 | | Comparison of Head Characteristics | | | | Maturity Date: | |
|---|---|---|---|---|---|---|---|---|
| Wet Date: | 7/31/ | Location: | Blanco | Ranch/lot: Dave McFad | | | 1 Icon | ######## |
| Date evald: | 10/8/ | Grower: | T&A | Commercial variety: Sharpshoote | | | 2 Pybas 251 | ######## |

| | Core length (cm) | | Core diam. (cm) | | Head diam. (cm) | | Head length (cm) | |
|---|---|---|---|---|---|---|---|---|
| Sample # | Icon | Pybas 251 | Icon | Pybas 251 | Icon | Pybas 251 | Icon | Pybas 251 |
| 1 | 4.9 | 4.2 | 3.9 | 3.5 | 19.0 | 16.1 | 16.0 | 14.2 |
| 2 | 4.5 | 4.6 | 4.2 | 3.8 | 17.4 | 18.9 | 15.8 | 17.6 |
| 3 | 3.4 | 4.9 | 3.5 | 3.5 | 18.6 | 19.5 | 17.6 | 21.3 |
| 4 | 3.5 | 5.1 | 3.8 | 3.5 | 18.2 | 17.5 | 14.9 | 19.5 |
| 5 | 4.1 | 3.5 | 3.6 | 3.6 | 17.9 | 17.9 | 16.4 | 19.2 |
| 6 | 4.2 | 3.5 | 4.0 | 3.9 | 19.2 | 16.8 | 17.2 | 18.2 |
| 7 | 3.4 | 5.9 | 3.6 | 3.6 | 17.4 | 16.6 | 14.6 | 18.2 |
| 8 | 4.1 | 5.2 | 3.6 | 3.8 | 15.6 | 16.5 | 15.4 | 17.8 |
| 9 | 4.2 | 4.9 | 3.9 | 3.6 | 15.2 | 15.9 | 15.6 | 18.0 |
| 10 | 4.4 | 4.6 | 3.6 | 3.7 | 18.5 | 16.2 | 16.6 | 16.8 |
| 11 | 3.2 | 5.2 | 3.9 | 4.0 | 15.9 | 17.0 | 15.9 | 19.4 |
| 12 | 4.9 | 5.2 | 3.9 | 4.0 | 18.6 | 18.0 | 18.6 | 18.0 |
| 13 | 5.4 | 4.2 | 4.0 | 4.0 | 15.7 | 16.6 | 15.9 | 17.5 |
| 14 | 4.6 | 4.1 | 3.5 | 3.5 | 18.2 | 16.9 | 19.1 | 17.5 |
| 15 | 3.5 | 4.6 | 3.6 | 3.6 | 16.6 | 16.0 | 16.6 | 14.5 |

TABLE 9-continued

| Trial map #: | SVPD99003 | | Comparison of Head Characteristics | | | Maturity Date: | |
|---|---|---|---|---|---|---|---|
| Wet Date: | 7/31/ | Location: | Blanco | Ranch/lot: Dave McFad | | 1 Icon | ####### |
| Date evald: | 10/8/ | Grower: | T&A | Commercial variety: Sharpshoote | | 2 Pybas 251 | ####### |
| 16 | 4.0 | 3.6 | 3.6 | 3.9 | 15.2 | 18.4 | 17.5 | 19.2 |
| 17 | 2.8 | 5.2 | 3.2 | 3.5 | 16.9 | 16.9 | 16.9 | 18.2 |
| 18 | 3.2 | 4.1 | 3.5 | 3.6 | 15.2 | 16.5 | 15.6 | 14.2 |
| 19 | 3.4 | 4.1 | 3.6 | 3.5 | 16.6 | 17.8 | 16.5 | 15.6 |
| 20 | 4.0 | 5.4 | 3.6 | 3.4 | 15.9 | 15.5 | 16.9 | 16.8 |
| 21 | 4.9 | 4.5 | 3.5 | 3.2 | 14.8 | 17.5 | 15.9 | 19.2 |
| 22 | 4.4 | 5.2 | 3.6 | 3.6 | 16.1 | 15.3 | 14.5 | 17.2 |
| 23 | 5.6 | 4.2 | 3.7 | 4.0 | 17.2 | 15.6 | 16.6 | 17.2 |
| 24 | 3.0 | 6.0 | 3.7 | 3.8 | 16.9 | 19.1 | 16.6 | 17.0 |
| Average | 4.1 | 4.7 | 3.7 | 3.7 | 17.0 | 17.0 | 16.4 | 17.6 |
| Stan dev | 0.7568049 | 0.693865 | 0.218526 | 0.217854 | 1.351006 | 1.156801 | 1.11771 | 1.7241202 |
| 300 | 0.0063022 | | 0.742213 | | 0.801789 | | 0.005845 | |

| | Avg Head Diameter (cm | | Avg Head Diam: Core | | Frame diam (cm) | | Head wt. (g) | |
|---|---|---|---|---|---|---|---|---|
| Sample # | Icon | Pybas 251 | Icon | Pybas 251 | Icon | Pybas 251 | Icon | Pybas 251 |
| 1 | 17.5 | 15.2 | 3.6 | 3.6 | 51 | 48 | 878 | 1170 |
| 2 | 16.6 | 18.3 | 3.7 | 4.0 | 53 | 52 | 908 | 918 |
| 3 | 18.1 | 20.4 | 5.3 | 4.2 | 49 | 51 | 870 | 710 |
| 4 | 16.6 | 18.5 | 4.7 | 3.6 | 51 | 48 | 906 | 850 |
| 5 | 17.2 | 18.6 | 4.2 | 3.6 | 53 | 54 | 868 | 724 |
| 6 | 18.2 | 17.5 | 4.3 | 5.0 | 51 | 52 | 914 | 986 |
| 7 | 16.0 | 17.4 | 4.7 | 5.0 | 51 | 51 | 884 | 1142 |
| 8 | 15.5 | 17.2 | 3.8 | 2.9 | 53 | 53 | 736 | 928 |
| 9 | 15.4 | 17.0 | 3.7 | 3.3 | 52 | 52 | 828 | 1146 |
| 10 | 17.6 | 16.5 | 4.0 | 3.4 | 53 | 49 | 866 | 796 |
| 11 | 15.9 | 18.2 | 5.0 | 4.0 | 54 | 49 | 968 | 1144 |
| 12 | 18.6 | 18.0 | 3.8 | 3.5 | 49 | 47 | 842 | 900 |
| 13 | 15.8 | 17.1 | 2.9 | 3.3 | 55 | 50 | 1126 | 788 |
| 14 | 18.7 | 17.2 | 4.1 | 4.1 | 51 | 51 | 826 | 856 |
| 15 | 16.6 | 15.3 | 4.7 | 3.7 | 52 | 47 | 884 | 868 |
| 16 | 16.4 | 18.8 | 4.1 | 4.1 | 53 | 51 | 822 | 1107 |
| 17 | 16.9 | 17.6 | 6.0 | 3.4 | 51 | 53 | 804 | 934 |
| 18 | 15.4 | 15.4 | 4.8 | 3.7 | 52 | 53 | 814 | 806 |
| 19 | 16.6 | 16.7 | 4.9 | 4.1 | 53 | 52 | 866 | 816 |
| 20 | 16.4 | 16.2 | 4.1 | 3.0 | 52 | 55 | 834 | 1020 |
| 21 | 15.4 | 18.4 | 3.1 | 4.1 | 49 | 52 | 943 | 988 |
| 22 | 15.3 | 16.3 | 3.5 | 3.1 | 53 | 54 | 1020 | 988 |
| 23 | 16.9 | 16.4 | 3.0 | 3.9 | 53 | 55 | 888 | 826 |
| 24 | 16.8 | 18.1 | 5.6 | 3.0 | 51 | 55 | 772 | 696 |
| Average | 16.7 | 17.3 | 4.2 | 3.7 | 51.9 | 51.4 | 878.3 | 921.1 |
| Stan dev | 1.0228548 | 1.2495923 | 0.8030308 | 0.5468848 | 1.5411 | 2.44801 | 81.21108 | 144.77608 |
| 300 | 0.0439089 | | 0.0139426 | | 0.44159 | | 0.212122 | |

TABLE 10

| Trial map #: | PD00007 | | Comparison of Head Characteristics | | | Maturity Date: | |
|---|---|---|---|---|---|---|---|
| Wet Date: | 5/24/ | Location: | Salinas | Ranch/lot: Martella/6 | | 1 Pybas 251 | 7/30/ |
| Date evald: | 7/27/ | Grower: | Bengard | Commerci Venus | | 2 Icon | 7/30/ |

| | Core length (cm) | | Core diam. (cm) | | Head diam. (cm) | | Head length (cm) | |
|---|---|---|---|---|---|---|---|---|
| Sample # | Pybas 251 | Icon | Pybas 251 | Icon | Pybas 251 | Icon | Pybas 251 | Icon |
| 1 | 5.1 | 2.5 | 4.1 | 3.9 | 16.5 | 12.9 | 17.0 | 13.3 |
| 2 | 3.9 | 2.9 | 4.3 | 3.5 | 13.5 | 14.9 | 15.2 | 15.1 |
| 3 | 3.9 | 2.9 | 3.9 | 3.4 | 15.2 | 13.1 | 17.1 | 15.1 |
| 4 | 4.9 | 4.1 | 3.5 | 3.7 | 16.0 | 13.5 | 16.3 | 15.1 |
| 5 | 5.1 | 2.9 | 4.3 | 3.9 | 16.5 | 15.5 | 16.9 | 15.7 |
| 6 | 2.9 | 3.9 | 4.5 | 3.5 | 14.5 | 16.1 | 14.5 | 15.5 |
| 7 | 3.9 | 3.9 | 4.1 | 4.1 | 14.3 | 11.9 | 15.9 | 13.9 |
| 8 | 5.1 | 2.9 | 4.3 | 3.6 | 14.1 | 14.1 | 18.1 | 13.5 |
| 9 | 4.3 | 4.1 | 4.0 | 3.7 | 15.6 | 12.5 | 16.1 | 13.7 |
| 10 | 5.6 | 3.9 | 4.1 | 3.9 | 15.1 | 13.7 | 19.9 | 14.1 |
| 11 | 5.9 | 3.9 | 4.2 | 4.1 | 15.6 | 15.9 | 16.1 | 14.7 |
| 12 | 4.1 | 3.9 | 4.3 | 3.9 | 16.1 | 15.5 | 16.9 | 15.2 |
| 13 | 5.1 | 2.5 | 4.1 | 3.8 | 14.9 | 15.5 | 16.9 | 13.2 |
| 14 | 4.9 | 2.3 | 3.9 | 3.5 | 16.0 | 13.9 | 15.5 | 15.5 |

TABLE 10-continued

| Trial map #: | PD00007 | | Comparison of Head Characteristics | | | | Maturity Date: | |
|---|---|---|---|---|---|---|---|---|
| Wet Date: | 5/24/ | Location: | Salinas | Ranch/lot: Martella/6 | | 1 Pybas 251 | 7/30/ | |
| Date evald: | 7/27/ | Grower: | Bengard | Commerci Venus | | 2 Icon | 7/30/ | |
| 15 | 4.1 | 3.9 | 3.8 | 3.7 | 15.5 | 15.1 | 16.1 | 14.5 |
| 16 | 4.2 | 3.2 | 4.1 | 3.4 | 16.1 | 14.1 | 15.9 | 13.9 |
| 17 | 4.3 | 4.1 | 3.9 | 2.9 | 17.5 | 14.6 | 17.1 | 14.9 |
| 18 | 3.9 | 3.6 | 3.5 | 3.6 | 13.5 | 13.2 | 14.1 | 14.1 |
| 19 | 4.3 | 2.9 | 4.5 | 3.7 | 16.1 | 13.7 | 17.2 | 12.6 |
| 20 | 4.1 | 3.2 | 3.9 | 4.1 | 15.2 | 12.9 | 16.9 | 12.1 |
| 21 | 4.3 | 3.6 | 4.1 | 3.9 | 16.1 | 15.2 | 18.1 | 13.5 |
| 22 | 3.1 | 3.9 | 4.2 | 4.2 | 15.1 | 15.1 | 15.5 | 13.1 |
| 23 | 3.9 | 3.9 | 4.3 | 3.8 | 16.1 | 14.1 | 15.9 | 15.6 |
| 24 | 4.4 | 3.4 | 4.3 | 3.6 | 15.4 | 14.2 | 16.5 | 14.3 |
| Average | 4.4 | 3.4 | 4.1 | 3.7 | 15.4 | 14.2 | 16.5 | 14.3 |
| Stan dev | 0.7128098 | 0.578213 | 0.260295 | 0.287795 | 0.966757 | 1.136611 | 1.212727 | 1.004302 |
| T test | 5.97E−06 | | 3.02E−05 | | 2.22E−04 | | 1.14E−08 | |

| | Avg Head Diameter (cm) | | Avg Head Diam: Core | | Frame diam (cm) | | Head wt. (g) | |
|---|---|---|---|---|---|---|---|---|
| Sample # | Pybas 251 | Icon | Pybas 251 | Icon | Pybas 251 | Icon | Pybas 251 | Icon |
| 1 | 16.8 | 13.1 | 3.3 | 5.2 | 58 | 52 | 907 | 592 |
| 2 | 14.4 | 15.0 | 3.7 | 5.2 | 55 | 50 | 758 | 865 |
| 3 | 16.2 | 14.1 | 4.1 | 4.9 | 54 | 51 | 837 | 945 |
| 4 | 16.2 | 14.3 | 3.3 | 3.5 | 55 | 52 | 898 | 933 |
| 5 | 16.7 | 15.6 | 3.3 | 3.8 | 54 | 54 | 1141 | 847 |
| 6 | 14.5 | 15.8 | 5.0 | 5.4 | 56 | 51 | 1122 | 765 |
| 7 | 15.1 | 12.9 | 3.9 | 3.3 | 54 | 52 | 881 | 842 |
| 8 | 16.1 | 13.8 | 3.2 | 3.5 | 57 | 56 | 814 | 672 |
| 9 | 15.9 | 13.1 | 3.7 | 4.5 | 56 | 51 | 1046 | 821 |
| 10 | 17.5 | 13.9 | 3.1 | 3.4 | 56 | 51 | 875 | 560 |
| 11 | 15.9 | 15.3 | 2.7 | 3.9 | 55 | 55 | 738 | 765 |
| 12 | 16.5 | 15.4 | 4.0 | 3.9 | 57 | 49 | 839 | 896 |
| 13 | 15.9 | 14.4 | 3.1 | 3.7 | 56 | 51 | 837 | 918 |
| 14 | 15.8 | 14.7 | 3.2 | 5.9 | 55 | 52 | 852 | 597 |
| 15 | 15.8 | 14.8 | 3.9 | 6.4 | 56 | 53 | 857 | 579 |
| 16 | 16.0 | 14.0 | 3.6 | 3.6 | 56 | 53 | 841 | 783 |
| 17 | 17.3 | 14.8 | 4.0 | 3.6 | 58 | 51 | 934 | 827 |
| 18 | 13.8 | 13.7 | 3.5 | 3.8 | 53 | 53 | 919 | 566 |
| 19 | 16.7 | 13.2 | 3.9 | 4.5 | 54 | 52 | 1030 | 783 |
| 20 | 16.1 | 12.5 | 3.9 | 3.9 | 57 | 50 | 1029 | 912 |
| 21 | 17.1 | 14.4 | 4.0 | 4.0 | 53 | 54 | 1035 | 915 |
| 22 | 15.3 | 14.1 | 4.9 | 3.6 | 55 | 49 | 768 | 676 |
| 23 | 16.0 | 14.9 | 4.1 | 3.8 | 53 | 55 | 901 | 744 |
| 24 | 16.0 | 14.3 | 3.6 | 4.2 | 56 | 53 | 889 | 655 |
| Average | 16.0 | 14.2 | 3.7 | 4.2 | 55.4 | 52.1 | 906.2 | 769.1 |
| Stan dev | 0.88885 | 0.8788889 | 0.5425605 | 0.8475916 | 1.468880082 | 1.839581 | 108.8943 | 128.3118 |
| T test | 2.08E−08 | | 1.52E−02 | | 1.53E−08 | | 2.35E−04 | |

TABLE 11

| Trial map #: | PD00007 | | Comparison of Head Characteristics | | | | Maturity Date: | |
|---|---|---|---|---|---|---|---|---|
| Wet Date: | 5/24/ | Location: | Salinas | Ranch/lot: Martella/6 | | 1 Spector | 7/30/ | |
| Date evald: | 7/27/ | Grower: | Bengard | Commerci Venus | | 2 Icon | 7/30/ | |
| | Core length (cm) | | Core diam. (cm) | | Head diam. (cm) | | Head length (cm) | |
| Sample # | Spector | Icon | Spector | Icon | Spector | Icon | Spector | Icon |
| 1 | 3.1 | 2.5 | 3.6 | 3.9 | 15.1 | 12.9 | 16.9 | 13.3 |
| 2 | 5.9 | 2.9 | 4.1 | 3.5 | 16.5 | 14.9 | 17.6 | 15.1 |
| 3 | 4.3 | 2.9 | 4.2 | 3.4 | 13.1 | 13.1 | 13.9 | 15.1 |
| 4 | 4.1 | 4.1 | 3.9 | 3.7 | 14.5 | 13.5 | 16.2 | 15.1 |
| 5 | 3.3 | 2.9 | 4.2 | 3.9 | 12.9 | 15.5 | 14.1 | 15.7 |
| 6 | 3.5 | 3.9 | 3.5 | 3.5 | 12.9 | 16.1 | 14.9 | 15.5 |
| 7 | 2.9 | 3.9 | 3.9 | 4.1 | 11.5 | 11.9 | 12.6 | 13.9 |
| 8 | 3.9 | 2.9 | 4.1 | 3.6 | 15.6 | 14.1 | 16.3 | 13.5 |
| 9 | 2.9 | 4.1 | 3.6 | 3.7 | 11.9 | 12.5 | 13.1 | 13.7 |
| 10 | 4.1 | 3.9 | 3.7 | 3.9 | 13.5 | 13.7 | 15.1 | 14.1 |
| 11 | 3.5 | 3.9 | 3.5 | 4.1 | 13.9 | 15.9 | 15.9 | 14.7 |
| 12 | 2.9 | 3.9 | 3.7 | 3.9 | 14.1 | 15.5 | 14.5 | 15.2 |
| 13 | 2.6 | 2.5 | 3.9 | 3.8 | 12.5 | 15.5 | 13.9 | 13.2 |

TABLE 11-continued

| Trial map #: | PD00007 | | Comparison of Head Characteristics | | | | Maturity Date: | |
|---|---|---|---|---|---|---|---|---|
| Wet Date: | 5/24/ | Location: | Salinas | Ranch/lot: Martella/6 | | 1 Spector | 7/30/ | |
| Date evald: | 7/27/ | Grower: | Bengard | Commerci Venus | | 2 Icon | 7/30/ | |
| 14 | 3.7 | 2.3 | 3.6 | 3.5 | 13.5 | 13.9 | 14.9 | 15.5 |
| 15 | 3.9 | 3.9 | 3.5 | 3.7 | 13.9 | 15.1 | 14.6 | 14.5 |
| 16 | 4.5 | 3.2 | 3.7 | 3.4 | 15.3 | 14.1 | 13.9 | 13.9 |
| 17 | 4.9 | 4.1 | 4.1 | 2.9 | 16.2 | 14.6 | 15.9 | 14.9 |
| 18 | 5.2 | 3.6 | 3.9 | 3.6 | 12.9 | 13.2 | 14.7 | 14.1 |
| 19 | 4.2 | 2.9 | 3.4 | 3.7 | 15.1 | 13.7 | 14.9 | 12.6 |
| 20 | 5.6 | 3.2 | 3.9 | 4.1 | 15.6 | 12.9 | 14.7 | 12.1 |
| 21 | 2.9 | 3.6 | 3.6 | 3.9 | 14.1 | 15.2 | 14.5 | 13.5 |
| 22 | 3.9 | 3.9 | 4.2 | 4.2 | 16.9 | 15.1 | 15.9 | 13.1 |
| 23 | 3.2 | 3.9 | 4.1 | 3.8 | 14.9 | 14.1 | 15.5 | 15.6 |
| 24 | 3.9 | 3.4 | 4.3 | 3.6 | 16.1 | 14.2 | 15.6 | 14.3 |
| Average | 3.9 | 3.4 | 3.8 | 3.7 | 14.3 | 14.2 | 15.0 | 14.3 |
| Stan dev | 0.8794658 | 0.578213 | 0.273332 | 0.287795 | 1.479271 | 1.136611 | 1.16525 | 1.004302 |
| T test | 4.55E−02 | | 1.57E−01 | | 8.88E−01 | | 2.18E−02 | |

| | Avg Head Diameter (cm | | Avg Head Diam: Core | | Frame diam (cm) | | Head wt. (g) | |
|---|---|---|---|---|---|---|---|---|
| Sample # | Spector | Icon | Spector | Icon | Spector | Icon | Spector | Icon |
| 1 | 16.0 | 13.1 | 5.2 | 5.2 | 49 | 52 | 840 | 592 |
| 2 | 17.1 | 15.0 | 2.9 | 5.2 | 53 | 50 | 1025 | 865 |
| 3 | 13.5 | 14.1 | 3.1 | 4.9 | 50 | 51 | 801 | 945 |
| 4 | 15.4 | 14.3 | 3.7 | 3.5 | 45 | 52 | 803 | 933 |
| 5 | 13.5 | 15.6 | 4.1 | 3.8 | 53 | 54 | 895 | 847 |
| 6 | 13.9 | 15.8 | 4.0 | 5.4 | 49 | 51 | 911 | 765 |
| 7 | 12.1 | 12.9 | 4.2 | 3.3 | 48 | 52 | 633 | 842 |
| 8 | 16.0 | 13.8 | 4.1 | 3.5 | 49 | 56 | 740 | 672 |
| 9 | 12.5 | 13.1 | 4.3 | 4.5 | 53 | 51 | 1003 | 821 |
| 10 | 14.3 | 13.9 | 3.5 | 3.4 | 49 | 51 | 836 | 560 |
| 11 | 14.9 | 15.3 | 4.3 | 3.9 | 48 | 55 | 948 | 765 |
| 12 | 14.3 | 15.4 | 4.9 | 3.9 | 52 | 49 | 585 | 896 |
| 13 | 13.2 | 14.4 | 5.1 | 3.7 | 52 | 51 | 750 | 918 |
| 14 | 14.2 | 14.7 | 3.8 | 5.9 | 49 | 52 | 935 | 597 |
| 15 | 14.3 | 14.8 | 3.7 | 6.4 | 47 | 53 | 816 | 579 |
| 16 | 14.6 | 14.0 | 3.2 | 3.6 | 50 | 53 | 1091 | 783 |
| 17 | 16.1 | 14.8 | 3.3 | 3.6 | 55 | 51 | 671 | 827 |
| 18 | 13.8 | 13.7 | 2.7 | 3.8 | 53 | 53 | 1144 | 566 |
| 19 | 15.0 | 13.2 | 3.6 | 4.5 | 49 | 52 | 852 | 783 |
| 20 | 15.2 | 12.5 | 2.7 | 3.9 | 51 | 50 | 1091 | 912 |
| 21 | 14.3 | 14.4 | 4.9 | 4.0 | 49 | 54 | 856 | 915 |
| 22 | 16.4 | 14.1 | 4.2 | 3.6 | 51 | 49 | 874 | 676 |
| 23 | 15.2 | 14.9 | 4.8 | 3.8 | 54 | 55 | 695 | 744 |
| 24 | 15.9 | 14.3 | 4.1 | 4.2 | 46 | 53 | 828 | 655 |
| Average | 14.6 | 14.2 | 3.9 | 4.2 | 50.2 | 52.1 | 859.3 | 769.1 |
| Stan dev | 1.2354589 | 0.8788889 | 0.7263238 | 0.8475916 | 2.565094568 | 1.839581 | 144.4295 | 128.3118 |
| T test | 2.03E−01 | | 1.80E−01 | | 4.66E−03 | | 2.68E−02 | |

TABLE 12

| Trial map #: | YM99219 | | Comparison of Head Characteristics | | | | Maturity Date: | |
|---|---|---|---|---|---|---|---|---|
| Wet Date: | 12/10/ | Location: | Dome Valley | Ranch/lot: Monkey/6-A | | 1 Icon | 3/24/ | |
| Date evald: | 3/25/ | Grower: | Mission | Commercial Var Headmaste | | 2 Spector | 3/24/ | |

| | Core length (cm) | | Core diam. (cm) | | Head diam. (cm) | | Head length (cm) | |
|---|---|---|---|---|---|---|---|---|
| Sample # | Icon | Spector | Icon | Spector | Icon | Spector | Icon | Spector |
| 1 | 6.1 | 5.5 | 5.0 | 4.1 | 18.7 | 17.2 | 18.2 | 16.5 |
| 2 | 4.5 | 4.2 | 5.0 | 4.5 | 19.5 | 18.2 | 18.6 | 16.6 |
| 3 | 5.0 | 4.5 | 4.6 | 4.8 | 18.9 | 15.4 | 18.4 | 16.8 |
| 4 | 6.5 | 3.2 | 4.7 | 4.6 | 17.8 | 15.8 | 18.7 | 14.4 |
| 5 | 6.2 | 4.7 | 4.6 | 5.0 | 17.5 | 16.9 | 16.7 | 16.4 |
| 6 | 4.2 | 5.6 | 4.7 | 4.7 | 15.3 | 17.0 | 15.4 | 17.6 |
| 7 | 6.0 | 6.0 | 4.9 | 4.7 | 18.0 | 15.9 | 17.4 | 15.0 |
| 8 | 4.0 | 4.2 | 4.3 | 4.3 | 17.5 | 14.9 | 18.0 | 16.7 |
| 9 | 5.8 | 5.5 | 5.0 | 4.9 | 17.4 | 16.0 | 15.0 | 16.0 |
| 10 | 5.4 | 6.2 | 4.8 | 5.2 | 18.1 | 17.5 | 19.7 | 16.3 |
| 11 | 6.2 | 4.0 | 5.0 | 4.2 | 19.1 | 14.7 | 16.5 | 16.1 |
| 12 | 5.4 | 4.1 | 4.7 | 4.5 | 17.7 | 16.0 | 18.0 | 15.2 |

TABLE 12-continued

| Trial map #: | YM99219 | | Comparison of Head Characteristics | | | | Maturity Date: | |
|---|---|---|---|---|---|---|---|---|
| Wet Date: | 12/10/ | Location: | Dome Valley | Ranch/lot: Monkey/6-A | | 1 Icon | 3/24/ | |
| Date evald: | 3/25/ | Grower: | Mission | Commercial Var Headmaste | | 2 Spector | 3/24/ | |

| | | | | | | | | |
|---|---|---|---|---|---|---|---|---|
| 13 | 5.2 | 6.0 | 4.5 | 4.5 | 14.4 | 17.5 | 15.6 | 14.0 |
| 14 | 5.7 | 5.2 | 5.5 | 5.1 | 18.2 | 16.2 | 16.7 | 16.2 |
| 15 | 5.6 | 4.4 | 3.6 | 4.5 | 20.6 | 19.3 | 16.1 | 18.0 |
| 16 | 4.9 | 3.0 | 4.3 | 4.2 | 17.4 | 13.5 | 16.7 | 16.5 |
| 17 | 4.8 | 3.2 | 4.7 | 4.7 | 14.7 | 16.5 | 15.7 | 15.2 |
| 18 | 4.2 | 5.6 | 4.5 | 4.2 | 17.5 | 18.9 | 17.4 | 17.7 |
| 19 | 3.5 | 5.0 | 4.4 | 4.0 | 18.7 | 17.0 | 16.5 | 15.7 |
| 20 | 5.5 | 6.0 | 4.3 | 4.7 | 16.2 | 18.7 | 15.5 | 16.7 |
| 21 | 4.9 | 5.7 | 4.6 | 4.7 | 18.2 | 18.0 | 16.4 | 16.9 |
| 22 | 5.7 | 4.5 | 4.5 | 4.6 | 16.1 | 17.3 | 16.4 | 16.8 |
| 23 | 3.9 | 4.7 | 4.4 | 4.2 | 15.5 | 16.9 | 16.0 | 14.7 |
| 24 | 3.0 | 4.9 | 4.9 | 4.5 | 18.4 | 16.3 | 17.3 | 15.3 |
| Average | 5.1 | 4.8 | 4.6 | 4.6 | 17.6 | 16.7 | 17.0 | 16.1 |
| Stan dev | 0.9273228 | 0.935056 | 0.363532 | 0.316113 | 1.523987 | 1.378615 | 1.22047 | 1.028639 |
| T test | 3.34E−01 | | 3.78E−01 | | 5.53E−02 | | 1.58E−02 | |

| | Avg Head Diameter (cm) | | Avg Head Diam: Core | | Frame diam (cm) | | Head wt. (g) | |
|---|---|---|---|---|---|---|---|---|
| Sample # | Icon | Spector | Icon | Spector | Icon | Spector | Icon | Spector |
| 1 | 18.5 | 16.9 | 3.0 | 3.1 | 55 | 51 | 1825 | 1298 |
| 2 | 19.1 | 17.4 | 4.2 | 4.1 | 54 | 56 | 1223 | 1266 |
| 3 | 18.7 | 16.1 | 3.7 | 3.6 | 52 | 51 | 1643 | 1396 |
| 4 | 18.3 | 15.1 | 2.8 | 4.7 | 51 | 50 | 1591 | 1221 |
| 5 | 17.1 | 16.7 | 2.8 | 5.2 | 52 | 54 | 1168 | 1264 |
| 6 | 15.4 | 17.3 | 3.7 | 3.7 | 56 | 53 | 1382 | 790 |
| 7 | 17.7 | 15.5 | 3.0 | 2.8 | 52 | 53 | 1256 | 1389 |
| 8 | 17.8 | 15.8 | 4.4 | 2.6 | 58 | 52 | 1499 | 1316 |
| 9 | 16.2 | 16.0 | 2.8 | 3.8 | 55 | 58 | 1077 | 1921 |
| 10 | 18.9 | 16.9 | 3.5 | 3.1 | 49 | 53 | 1008 | 1378 |
| 11 | 17.8 | 15.4 | 2.9 | 2.5 | 57 | 54 | 1673 | 1231 |
| 12 | 17.9 | 15.6 | 3.3 | 3.9 | 55 | 54 | 1168 | 1316 |
| 13 | 15.0 | 15.8 | 2.9 | 3.8 | 56 | 54 | 1827 | 1080 |
| 14 | 17.5 | 16.2 | 3.1 | 2.7 | 57 | 53 | 1839 | 876 |
| 15 | 18.4 | 18.7 | 3.3 | 3.6 | 55 | 53 | 1778 | 1665 |
| 16 | 17.1 | 15.0 | 3.5 | 3.4 | 50 | 50 | 1843 | 1431 |
| 17 | 15.2 | 15.9 | 3.2 | 5.0 | 56 | 46 | 1432 | 1102 |
| 18 | 17.5 | 18.3 | 4.2 | 3.3 | 56 | 50 | 1584 | 1338 |
| 19 | 17.6 | 16.4 | 5.0 | 3.3 | 57 | 50 | 1763 | 1057 |
| 20 | 15.9 | 17.7 | 2.9 | 3.0 | 56 | 50 | 1724 | 1386 |
| 21 | 17.3 | 17.5 | 3.5 | 3.1 | 58 | 54 | 1604 | 1407 |
| 22 | 16.3 | 17.1 | 2.9 | 3.8 | 59 | 52 | 1388 | 1193 |
| 23 | 15.8 | 15.8 | 4.0 | 3.4 | 47 | 54 | 1931 | 812 |
| 24 | 17.9 | 15.8 | 6.0 | 3.2 | 50 | 53 | 1541 | 1023 |
| Average | 17.3 | 16.4 | 3.5 | 3.5 | 54.3 | 52.4 | 1532.0 | 1256.5 |
| Stan dev | 1.1887436 | 0.9884638 | 0.7960187 | 0.7057176 | 3.182549794 | 2.430185 | 271.0698 | 252.0304 |
| T test | 1.25E−02 | | 9.86E−01 | | 2.64E−02 | | 6.76E−04 | |

TABLE 13

| Trial map #: | PD99034 | | Comparison of Head Characteristics | | | | | |
|---|---|---|---|---|---|---|---|---|
| Wet Date: | 11/22/ | Location: | Bard | | Ranch/lot: E Berryman/11 | | | |
| Date evald: | 3/8/ | Grower: | Top Flavor | | Commercial Var Desert Spring | | | |

| | Core length (cm) | | Core diam. (cm) | | Head diam. (cm) | | Head length (cm) | |
|---|---|---|---|---|---|---|---|---|
| Sample # | Icon | Desert Spring | Icon | Desert Spring | Icon | Desert Spring | Icon | Desert Spring |
| 1 | 3.6 | 2.8 | 4.0 | 4.0 | 16.1 | 16.6 | 13.9 | 12.3 |
| 2 | 4.0 | 4.7 | 3.5 | 3.5 | 16.2 | 13.3 | 16.0 | 14.3 |
| 3 | 3.6 | 3.8 | 4.3 | 3.5 | 15.4 | 15.1 | 15.8 | 14.1 |
| 4 | 4.5 | 3.7 | 3.7 | 3.9 | 16.3 | 14.1 | 14.8 | 14.4 |
| 5 | 6.6 | 4.7 | 4.0 | 3.1 | 16.3 | 17.6 | 15.1 | 15.2 |
| 6 | 4.1 | 3.1 | 3.5 | 3.3 | 16.2 | 14.0 | 13.0 | 14.9 |
| 7 | 5.2 | 4.4 | 3.9 | 3.0 | 16.3 | 14.4 | 14.1 | 14.7 |
| 8 | 2.5 | 4.1 | 3.7 | 3.4 | 16.3 | 13.7 | 14.3 | 13.2 |
| 9 | 3.5 | 5.1 | 4.3 | 3.2 | 17.2 | 14.1 | 14.2 | 15.5 |
| 10 | 4.6 | 4.7 | 3.4 | 3.3 | 16.4 | 14.7 | 14.3 | 15.2 |
| 11 | 4.4 | 2.5 | 3.3 | 3.5 | 13.9 | 13.5 | 14.3 | 13.0 |

TABLE 13-continued

| Trial map #: | PD99034 | | | Comparison of Head Characteristics | | | | |
|---|---|---|---|---|---|---|---|---|
| Wet Date: | 11/22/ | | Location: | Bard | | Ranch/lot: E Berryman/11 | | |
| Date evald: | 3/8/ | | Grower: | Top Flavor | | Commercial Var Desert Spring | | |

| | | | | | | | | |
|---|---|---|---|---|---|---|---|---|
| 12 | 5.4 | 3.2 | 3.2 | 3.2 | 14.9 | 13.8 | 16.1 | 12.4 |
| 13 | 5.0 | 4.0 | 3.9 | 3.8 | 15.1 | 15.6 | 15.2 | 15.2 |
| 14 | 3.7 | 4.0 | 3.9 | 3.2 | 17.1 | 14.4 | 16.3 | 15.0 |
| 15 | 4.5 | 4.7 | 3.6 | 3.7 | 15.7 | 16.6 | 14.4 | 15.3 |
| 16 | 4.1 | 5.0 | 3.4 | 3.4 | 14.9 | 15.3 | 16.2 | 14.7 |
| 17 | 4.7 | 3.5 | 3.8 | 3.0 | 18.6 | 13.4 | 14.5 | 14.0 |
| 18 | 4.5 | 5.3 | 3.4 | 3.9 | 14.8 | 14.9 | 14.5 | 15.6 |
| 19 | 2.8 | 5.5 | 3.5 | 3.4 | 15.0 | 15.3 | 13.4 | 14.8 |
| 20 | 2.7 | 3.4 | 3.8 | 3.7 | 15.3 | 11.8 | 15.0 | 12.2 |
| 21 | 4.7 | 4.7 | 4.0 | 3.9 | 16.1 | 15.7 | 14.3 | 16.0 |
| 22 | 3.7 | 5.6 | 3.6 | 3.5 | 16.8 | 13.6 | 13.8 | 15.0 |
| 23 | 2.7 | 4.5 | 3.3 | 3.4 | 14.5 | 14.0 | 14.0 | 15.2 |
| 24 | 3.0 | 5.1 | 3.6 | 3.7 | 15.4 | 15.2 | 13.8 | 16.3 |
| Average | 4.1 | 4.3 | 3.7 | 3.5 | 15.9 | 14.6 | 14.6 | 14.5 |
| Stan dev | 0.9383052 | 0.862745449 | 0.30348221 | 0.293374915 | 1.0188086 | 1.265362124 | 0.9049682 | 1.143214068 |
| T test | 6.33E−01 | | 1.74E−02 | | 4.47E−04 | | 6.97E−01 | |

| | | Avg Head Diameter (cm | | Avg Head Diam: Core | | Frame diam (cm) | |
|---|---|---|---|---|---|---|---|
| | Sample # | Icon | Desert Spring | Icon | Desert Spring | Icon | Desert Spring |
| | 1 | 15.0 | 14.5 | 4.2 | 5.2 | 43 | 51 |
| | 2 | 16.1 | 13.8 | 4.0 | 2.9 | 49 | 44 |
| | 3 | 15.6 | 14.6 | 4.3 | 3.8 | 50 | 46 |
| | 4 | 15.6 | 14.3 | 3.5 | 3.9 | 54 | 53 |
| | 5 | 15.7 | 16.4 | 2.4 | 4.4 | 48 | 54 |
| | 6 | 14.6 | 14.5 | 3.6 | 3.1 | 52 | 50 |
| | 7 | 15.2 | 14.6 | 2.9 | 4.7 | 46 | 48 |
| | 8 | 15.3 | 13.5 | 6.1 | 3.1 | 47 | 54 |
| | 9 | 15.7 | 14.8 | 4.5 | 3.6 | 54 | 46 |
| | 10 | 15.4 | 15.0 | 3.3 | 2.9 | 55 | 45 |
| | 11 | 14.1 | 13.3 | 3.2 | 2.8 | 49 | 46 |
| | 12 | 15.5 | 13.1 | 2.9 | 5.2 | 54 | 47 |
| | 13 | 15.2 | 15.4 | 3.0 | 4.8 | 51 | 44 |
| | 14 | 16.7 | 14.7 | 4.5 | 3.7 | 49 | 47 |
| | 15 | 15.1 | 16.0 | 3.3 | 4.0 | 53 | 50 |
| | 16 | 15.6 | 15.0 | 3.8 | 3.2 | 54 | 50 |
| | 17 | 16.6 | 13.7 | 3.5 | 3.9 | 50 | 49 |
| | 18 | 14.7 | 15.3 | 3.3 | 2.9 | 47 | 45 |
| | 19 | 14.2 | 15.1 | 5.1 | 2.7 | 51 | 47 |
| | 20 | 15.2 | 12.0 | 4.1 | 3.5 | 52 | 53 |
| | 21 | 15.2 | 15.9 | 3.2 | 3.4 | 55 | 47 |
| | 22 | 15.3 | 14.3 | 4.1 | 2.6 | 52 | 52 |
| | 23 | 14.3 | 14.6 | 5.3 | 3.2 | 55 | |
| | 24 | 14.6 | 15.8 | 4.9 | 3.1 | 46 | 54 |
| | Average | 15.3 | 14.6 | 3.9 | 3.6 | 40.7 | 48.8 |
| | Stan dev | 0.6612701 | 1.0082989 | 0.8779036 | 0.7774654 | 3.34491 | 3.356899567 |
| | T test | 7.75E−03 | | 2.73E−01 | | 6.03E−02 | |

TABLE 14

| Trial map #: | YM99172 | | | Comparison of Head Characteristics | | | |
|---|---|---|---|---|---|---|---|
| Wet Date: | 11/6/ | | Location: | Dome Valley | | Ranch/lot: Powers 168 | |
| Date evald: | 3/7/ | | Grower: | Pasi | | Commercial Var Cibola | |

| | Core length (cm) | | Core diam. (cm) | | Head diam. (cm) | | Head length (cm) | |
|---|---|---|---|---|---|---|---|---|
| Sample # | Icon | Desert Spring | Icon | Desert Spring | Icon | Desert Spring | Icon | Desert Spring |
| 1 | 3.5 | 3.0 | 4.0 | 3.8 | 18.2 | 13.4 | 16.0 | 16.6 |
| 2 | 3.8 | 3.5 | 3.7 | 3.4 | 16.7 | 15.6 | 12.9 | 13.7 |
| 3 | 5.2 | 3.3 | 3.8 | 3.7 | 16.1 | 14.1 | 15.0 | 18.5 |
| 4 | 4.4 | 4.3 | 3.9 | 3.0 | 17.7 | 16.5 | 16.7 | 15.9 |
| 5 | 4.6 | 3.6 | 4.4 | 3.5 | 15.3 | 15.2 | 13.9 | 15.5 |
| 6 | 3.6 | 3.6 | 4.2 | 2.8 | 14.4 | 14.5 | 15.3 | 15.3 |
| 7 | 3.0 | 3.7 | 3.9 | 3.5 | 16.8 | 14.7 | 14.3 | 16.6 |
| 8 | 4.4 | 2.7 | 4.4 | 3.6 | 16.9 | 13.2 | 14.3 | 13.2 |
| 9 | 3.5 | 3.2 | 3.9 | 3.1 | 13.5 | 14.3 | 15.7 | 15.0 |
| 10 | 3.5 | 2.9 | 3.6 | 3.8 | 16.3 | 14.3 | 13.1 | 17.5 |
| 11 | 4.5 | 2.6 | 3.2 | 2.8 | 16.3 | 14.7 | 14.8 | 14.8 |

TABLE 14-continued

| Trial map #: | YM99172 | | | | Comparison of Head Characteristics | | | |
|---|---|---|---|---|---|---|---|---|
| Wet Date: | 11/6/ | | Location: | Dome Valley | | Ranch/lot: Powers 168 | | |
| Date evald: | 3/7/ | | Grower: | Pasi | | Commercial Var Cibola | | |

| | | | | | | | | |
|---|---|---|---|---|---|---|---|---|
| 12 | 3.4 | 4.7 | 3.3 | 3.3 | 16.4 | 15.7 | 13.0 | 15.4 |
| 13 | 2.7 | 4.6 | 4.3 | 3.5 | 16.1 | 14.5 | 14.8 | 16.7 |
| 14 | 2.9 | 4.0 | 3.8 | 3.4 | 17.8 | 14.6 | 15.1 | 16.9 |
| 15 | 4.6 | 2.8 | 3.7 | 3.7 | 15.5 | 15.7 | 14.6 | 17.4 |
| 16 | 3.2 | 2.7 | 4.1 | 3.5 | 15.2 | 15.3 | 14.5 | 15.9 |
| 17 | 2.6 | 5.5 | 3.2 | 3.9 | 16.0 | 14.2 | 15.3 | 17.4 |
| 18 | 3.2 | 3.6 | 4.1 | 3.1 | 14.3 | 13.4 | 15.4 | 14.1 |
| 19 | 4.4 | 4.0 | 3.8 | 3.9 | 17.1 | 13.5 | 15.8 | 14.9 |
| 20 | 4.0 | 5.0 | 4.0 | 3.4 | 15.3 | 16.4 | 15.5 | 15.0 |
| 21 | 4.3 | 3.8 | 3.8 | 3.2 | 15.0 | 14.6 | 15.4 | 16.8 |
| 22 | 4.5 | 3.7 | 3.9 | 3.4 | 16.1 | 17.4 | 15.9 | 16.2 |
| 23 | 3.9 | 3.7 | 3.9 | 3.4 | 15.1 | 15.4 | 14.9 | 15.7 |
| 24 | 3.0 | 3.1 | 4.0 | 3.5 | 16.3 | 18.0 | 15.1 | 16.5 |
| Average | 3.8 | 3.7 | 3.9 | 3.5 | 16.0 | 15.0 | 14.9 | 15.9 |
| Stan dev | 0.7077086 | 0.758144187 | 0.322327 | 0.286912601 | 1.141192 | 1.22675488 | 0.95567527 | 1.280448008 |
| T test | 5.45E−01 | | 3.44E−05 | | 3.58E−03 | | 3.38E−03 | |

| | Avg Head Diameter (cm | | Avg Head Diam: Core | | Frame diam (cm) | | Head wt. (g |
|---|---|---|---|---|---|---|---|
| Sample # | Icon | Desert Spring | Icon | Desert Spring | Icon | Desert Spring | Icon |
| 1 | 17.1 | 15.0 | 4.9 | 5.0 | 52 | 52 | 920 |
| 2 | 14.8 | 14.7 | 3.9 | 4.2 | 48 | 53 | 881 |
| 3 | 15.6 | 16.3 | 3.0 | 4.9 | 47 | 50 | 586 |
| 4 | 17.2 | 16.2 | 3.9 | 3.8 | 52 | 49 | 752 |
| 5 | 14.6 | 15.4 | 3.2 | 3.6 | 54 | 46 | 741 |
| 6 | 14.9 | 14.9 | 4.1 | 4.1 | 57 | 43 | 781 |
| 7 | 15.6 | 15.7 | 5.2 | 4.3 | 57 | 49 | 1018 |
| 8 | 15.6 | 13.2 | 3.5 | 3.6 | 55 | 44 | 815 |
| 9 | 14.6 | 14.7 | 4.2 | 5.4 | 53 | 46 | 751 |
| 10 | 14.7 | 15.9 | 4.2 | 5.0 | 53 | 51 | 997 |
| 11 | 15.6 | 14.8 | 3.5 | 5.1 | 60 | 51 | 860 |
| 12 | 14.7 | 15.6 | 4.3 | 6.0 | 52 | 48 | 778 |
| 13 | 15.5 | 15.6 | 5.7 | 3.3 | 60 | 53 | 625 |
| 14 | 16.5 | 15.8 | 5.7 | 3.4 | 52 | 47 | 863 |
| 15 | 15.1 | 16.6 | 3.3 | 4.1 | 53 | 51 | 932 |
| 16 | 14.9 | 15.6 | 4.6 | 5.6 | 57 | 50 | 901 |
| 17 | 16.7 | 15.8 | 6.0 | 2.9 | 57 | 57 | 886 |
| 18 | 14.9 | 13.8 | 4.6 | 3.8 | 54 | 54 | 881 |
| 19 | 16.5 | 14.2 | 3.7 | 3.6 | 50 | 53 | 1040 |
| 20 | 15.4 | 15.7 | 3.9 | 3.1 | 54 | 51 | 1103 |
| 21 | 15.2 | 15.7 | 3.5 | 4.1 | 50 | 54 | 845 |
| 22 | 16.0 | 16.8 | 3.6 | 4.5 | 53 | 54 | 976 |
| 23 | 15.0 | 15.6 | 3.8 | 4.2 | 52 | 49 | 859 |
| 24 | 15.7 | 17.3 | 5.2 | 5.6 | 48 | 51 | 1041 |
| Average | 15.5 | 15.4 | 4.2 | 4.3 | 53.3 | 50.3 | 868.0 |
| Stan dev | 0.7443233 | 0.9323664 | 0.8480283 | 0.8519719 | 3.459915 | 3.391164992 | 127.7086 |
| T test | 9.32E−01 | | 7.78E−01 | | 3.14E−03 | | 9.01E−02 |

TABLE 15

| Trial map #: | | | | Comparison of Head Characteristics | | | |
|---|---|---|---|---|---|---|---|
| Wet Date: | 11/23/ | | Location: | Dome Valley | | Ranch/lot: Moore 6 | |
| Date evald: | 3/10/ | | Grower: | Nakasawa | | Commercial V Desert Spring | |

| | Core length (cm) | | Core diam. (cm) | | Head diam. (cm) | | Head length (cm) | |
|---|---|---|---|---|---|---|---|---|
| Sample # | Icon | Desert Spring | Icon | Desert Spring | Icon | Desert Spring | Icon | Desert Spring |
| 1 | 3.0 | 5.1 | 4.2 | 3.4 | 15.0 | 15.3 | 13.9 | 14.5 |
| 2 | 3.0 | 3.5 | 4.1 | 3.6 | 17.8 | 15.2 | 16.0 | 13.6 |
| 3 | 4.7 | 4.2 | 3.5 | 3.4 | 16.6 | 13.6 | 14.7 | 13.6 |
| 4 | 3.5 | 6.0 | 4.0 | 3.7 | 15.7 | 14.0 | 13.4 | 15.1 |
| 5 | 4.0 | 7.0 | 4.0 | 3.3 | 16.4 | 13.8 | 16.5 | 15.0 |
| 6 | 5.5 | 4.3 | 4.0 | 3.6 | 16.2 | 13.2 | 14.8 | 14.2 |
| 7 | 5.0 | 5.5 | 4.2 | 3.5 | 13.6 | 14.3 | 15.2 | 13.6 |
| 8 | 4.8 | 4.4 | 3.9 | 3.7 | 16.2 | 15.0 | 15.5 | 12.6 |
| 9 | 3.1 | 6.5 | 4.2 | 3.5 | 16.0 | 15.2 | 15.4 | 13.5 |
| 10 | 3.3 | 4.5 | 4.3 | 3.6 | 16.4 | 15.0 | 14.8 | 13.3 |
| 11 | 3.1 | 5.0 | 3.7 | 3.7 | 16.1 | 14.2 | 15.5 | 14.2 |

TABLE 15-continued

| Trial map #: | | | | Comparison of Head Characteristics | | | | |
|---|---|---|---|---|---|---|---|---|
| Wet Date: | 11/23/ | | Location: | Dome Valley | | Ranch/lot: Moore 6 | | |
| Date evald: | 3/10/ | | Grower: | Nakasawa | | Commercial V Desert Spring | | |
| 12 | 3.2 | 5.1 | 3.7 | 3.5 | 17.4 | 13.2 | 16.0 | 13.4 |
| 13 | 3.5 | 4.5 | 3.6 | 3.2 | 15.1 | 15.2 | 15.7 | 13.2 |
| 14 | 3.2 | 4.0 | 4.1 | 3.4 | 15.8 | 15.5 | 14.0 | 14.7 |
| 15 | 3.7 | 3.9 | 3.9 | 3.4 | 14.7 | 15.3 | 13.3 | 14.2 |
| 16 | 3.7 | 4.3 | 3.7 | 3.4 | 14.5 | 15.6 | 15.7 | 13.8 |
| 17 | 4.5 | 5.2 | 4.2 | 3.5 | 17.3 | 14.3 | 13.3 | 13.7 |
| 18 | 3.5 | 4.4 | 3.6 | 3.5 | 16.6 | 13.9 | 14.2 | 14.5 |
| 19 | 4.0 | 4.3 | 4.4 | 3.5 | 18.3 | 14.7 | 16.0 | 14.3 |
| 20 | 4.9 | 4.6 | 4.3 | 3.6 | 16.0 | 15.6 | 15.0 | 13.7 |
| 21 | 3.2 | 6.3 | 3.8 | 3.4 | 14.4 | 14.8 | 14.9 | 13.4 |
| 22 | 3.5 | 5.0 | 3.9 | 3.5 | 14.3 | 14.3 | 14.0 | 14.1 |
| 23 | 5.0 | 4.3 | 3.5 | 3.5 | 16.8 | 13.9 | 15.3 | 14.6 |
| 24 | 3.0 | 4.5 | 3.3 | 3.5 | 16.4 | 15.7 | 15.3 | 13.3 |
| Average | 3.8 | 4.9 | 3.9 | 3.5 | 16.0 | 14.6 | 14.9 | 13.9 |
| Stan dev | 0.7787834 | 0.869782582 | 0.29632 | 0.123285341 | 1.1645737 | 0.773847905 | 0.917779298 | 0.621344382 |
| T test | 9.27E−05 | | 5.37E−08 | | 1.78E−05 | | 4.99E−05 | |

| | | Avg Head Diameter (cm) | | Avg Head Diam: Core | | Frame diam (cm) | |
|---|---|---|---|---|---|---|---|
| | Sample # | Icon | Desert Spring | Icon | Desert Spring | Icon | Desert Spring |
| | 1 | 14.5 | 14.9 | 4.8 | 2.9 | 51 | 46 |
| | 2 | 16.9 | 14.4 | 5.6 | 4.1 | 41 | 44 |
| | 3 | 15.7 | 13.6 | 3.3 | 3.2 | 46 | 45 |
| | 4 | 14.6 | 14.6 | 4.2 | 2.4 | 49 | 47 |
| | 5 | 16.5 | 14.4 | 4.1 | 2.4 | 46 | 46 |
| | 6 | 15.5 | 13.7 | 2.8 | 2.0 | 49 | 48 |
| | 7 | 14.4 | 14.0 | 2.9 | 3.2 | 49 | 44 |
| | 8 | 15.9 | 13.8 | 3.3 | 2.5 | 45 | 46 |
| | 9 | 15.7 | 14.4 | 4.1 | 3.3 | 46 | 45 |
| | 10 | 15.6 | 14.2 | 4.7 | 2.2 | 49 | 44 |
| | 11 | 15.8 | 14.2 | 5.1 | 3.2 | 49 | 44 |
| | 12 | 16.7 | 13.3 | 5.2 | 2.7 | 50 | 45 |
| | 13 | 15.4 | 14.2 | 4.4 | 2.8 | 47 | 43 |
| | 14 | 14.9 | 15.1 | 4.7 | 3.4 | 46 | 47 |
| | 15 | 14.0 | 14.8 | 3.8 | 3.7 | 50 | 47 |
| | 16 | 15.1 | 14.7 | 4.1 | 3.8 | 46 | 48 |
| | 17 | 15.3 | 14.0 | 3.4 | 2.7 | 48 | 45 |
| | 18 | 15.4 | 14.2 | 4.4 | 3.2 | 54 | 45 |
| | 19 | 17.2 | 14.5 | 4.3 | 3.4 | 49 | 45 |
| | 20 | 15.5 | 14.7 | 3.2 | 3.2 | 47 | 46 |
| | 21 | 14.7 | 14.1 | 4.6 | 2.2 | 47 | 42 |
| | 22 | 14.2 | 14.2 | 4.0 | 2.8 | 45 | 45 |
| | 23 | 16.1 | 14.3 | 3.2 | 3.3 | 53 | 43 |
| | 24 | 15.9 | 14.5 | 5.3 | 3.2 | 47 | 44 |
| | Average | 15.5 | 14.3 | 4.2 | 3.0 | 47.9 | 45.2 |
| | Stan dev | 0.8414101 | 0.4193195 | 0.8086789 | 0.5347297 | 2.755429 | 1.551063216 |
| | T test | 1.46E−07 | | 2.51E−07 | | 1.23E−04 | |

TABLE 16

| Trial map #: | SVPD99003 | | Comparison of Head Characteristics | | | Maturity Date: | |
|---|---|---|---|---|---|---|---|
| Wet Date: | 7/31/ | Location: | Blanco | Ranch/lot Dave McFad | | 1 Icon | ######## |
| Date evald: | 10/8/ | Grower: | T&A | Commercial con Sharpshoote | | 2 Spector | ######## |

| | Core length (cm) | | Core diam. (cm) | | Head diam. (cm) | | Head length (cm) | |
|---|---|---|---|---|---|---|---|---|
| Sample # | Icon | Spector | Icon | Spector | Icon | Spector | Icon | Spector |
| 1 | 4.9 | 3.7 | 3.9 | 3.1 | 19.0 | 17.2 | 18.0 | 15.5 |
| 2 | 4.5 | 4.2 | 4.2 | 4.0 | 17.4 | 16.4 | 15.8 | 14.9 |
| 3 | 3.4 | 3.5 | 3.5 | 3.9 | 18.6 | 16.2 | 17.6 | 14.8 |
| 4 | 3.5 | 3.1 | 3.8 | 3.5 | 18.2 | 14.5 | 14.9 | 17.3 |
| 5 | 4.1 | 3.4 | 3.6 | 3.5 | 17.9 | 15.9 | 16.4 | 14.4 |
| 6 | 4.2 | 4.9 | 4.0 | 3.6 | 19.2 | 16.6 | 17.2 | 14.5 |
| 7 | 3.4 | 3.6 | 3.6 | 3.5 | 17.4 | 15.2 | 14.6 | 13.8 |
| 8 | 4.1 | 3.9 | 3.6 | 3.6 | 15.6 | 17.5 | 15.4 | 16.2 |
| 9 | 4.2 | 4.1 | 3.9 | 3.8 | 15.2 | 16.3 | 15.6 | 15.5 |
| 10 | 4.4 | 4.1 | 3.6 | 3.2 | 18.5 | 14.4 | 16.6 | 16.4 |
| 11 | 3.2 | 4.4 | 3.9 | 3.6 | 15.9 | 16.2 | 15.9 | 14.0 |

TABLE 16-continued

| Trial map #: | SVPD99003 | | Comparison of Head Characteristics | | | | Maturity Date: | |
|---|---|---|---|---|---|---|---|---|
| Wet Date: | 7/31/ | Location: | Blanco | Ranch/lot Dave McFad | | | 1 Icon | ######## |
| Date evald: | 10/8/ | Grower: | T&A | Commercial con Sharpshoote | | | 2 Spector | ######## |
| 12 | 4.9 | 5.2 | 3.9 | 3.5 | 18.6 | 16.5 | 18.6 | 15.6 |
| 13 | 5.4 | 4.2 | 4.0 | 3.5 | 15.7 | 14.5 | 15.9 | 15.6 |
| 14 | 4.6 | 4.1 | 3.5 | 3.7 | 18.2 | 14.9 | 19.1 | 15.5 |
| 15 | 3.5 | 4.9 | 3.6 | 3.5 | 16.6 | 16.3 | 16.6 | 15.5 |
| 16 | 4.0 | 5.4 | 3.6 | 3.7 | 15.2 | 15.9 | 17.5 | 17.2 |
| 17 | 2.8 | 4.6 | 3.2 | 3.7 | 16.9 | 16.6 | 16.9 | 15.9 |
| 18 | 3.2 | 4.5 | 3.5 | 4.0 | 15.2 | 16.5 | 15.6 | 15.9 |
| 19 | 3.4 | 4.0 | 3.6 | 3.9 | 16.6 | 15.5 | 16.5 | 14.8 |
| 20 | 4.0 | 4.0 | 3.6 | 3.5 | 15.9 | 15.9 | 16.9 | 13.5 |
| 21 | 4.9 | 3.9 | 3.5 | 3.7 | 14.8 | 16.4 | 15.9 | 14.4 |
| 22 | 4.4 | 3.7 | 3.6 | 3.6 | 16.1 | 15.1 | 14.5 | 14.2 |
| 23 | 5.6 | 4.0 | 3.7 | 3.7 | 17.2 | 14.5 | 16.6 | 14.2 |
| 24 | 3.0 | 4.5 | 3.7 | 4.0 | 16.9 | 16.5 | 16.6 | 15.5 |
| Average | 4.1 | 4.2 | 3.7 | 3.6 | 17.0 | 15.9 | 16.4 | 15.2 |
| Stan dev | 0.7568049 | 0.56323 | 0.218526 | 0.228059 | 1.351 | 0.87798 | 1.11771 | 1.0014392 |
| T test | 0.6210953 | | 0.405178 | | 0.0025 | | 0.000396 | |

| Sample # | Avg Head Diameter (cm) | | Avg Head Diam: Core | | Frame diam (cm) | | Head wt. (g) | |
|---|---|---|---|---|---|---|---|---|
| | Icon | Spector | Icon | Spector | Icon | Spector | Icon | Spector |
| 1 | 17.5 | 16.4 | 3.6 | 4.4 | 51 | 49 | 878 | 1152 |
| 2 | 16.6 | 15.7 | 3.7 | 3.7 | 53 | 43 | 908 | 1158 |
| 3 | 18.1 | 15.5 | 5.3 | 4.4 | 49 | 48 | 870 | 852 |
| 4 | 16.6 | 15.9 | 4.7 | 5.1 | 51 | 49 | 906 | 820 |
| 5 | 17.2 | 15.2 | 4.2 | 4.9 | 53 | 51 | 868 | 1062 |
| 6 | 18.2 | 15.6 | 4.3 | 4.6 | 51 | 50 | 914 | 690 |
| 7 | 16.0 | 14.5 | 4.7 | 3.0 | 51 | 44 | 884 | 718 |
| 8 | 15.5 | 16.9 | 3.8 | 4.7 | 53 | 48 | 736 | 664 |
| 9 | 15.4 | 15.9 | 3.7 | 4.1 | 52 | 49 | 828 | 680 |
| 10 | 17.6 | 15.4 | 4.0 | 3.8 | 53 | 51 | 866 | 980 |
| 11 | 15.9 | 15.1 | 5.0 | 3.7 | 54 | 52 | 968 | 808 |
| 12 | 18.6 | 16.1 | 3.8 | 3.6 | 49 | 48 | 842 | 758 |
| 13 | 15.8 | 15.1 | 2.9 | 2.9 | 55 | 52 | 1126 | 832 |
| 14 | 18.7 | 15.2 | 4.1 | 3.6 | 51 | 48 | 826 | 748 |
| 15 | 16.6 | 15.9 | 4.7 | 3.9 | 52 | 53 | 884 | 904 |
| 16 | 16.4 | 16.6 | 4.1 | 3.4 | 53 | 47 | 822 | 926 |
| 17 | 16.9 | 16.3 | 6.0 | 3.5 | 51 | 47 | 804 | 842 |
| 18 | 15.4 | 16.2 | 4.8 | 3.6 | 52 | 49 | 814 | 740 |
| 19 | 16.6 | 15.2 | 4.9 | 3.8 | 53 | 44 | 866 | 812 |
| 20 | 16.4 | 14.7 | 4.1 | 3.7 | 52 | 47 | 834 | 660 |
| 21 | 15.4 | 15.4 | 3.1 | 3.9 | 49 | 51 | 954 | 882 |
| 22 | 15.3 | 14.7 | 3.5 | 4.0 | 53 | 44 | 1020 | 756 |
| 23 | 16.9 | 14.4 | 3.0 | 3.6 | 53 | 51 | 888 | 846 |
| 24 | 16.8 | 16.0 | 5.6 | 3.6 | 51 | 49 | 772 | 892 |
| Average | 16.7 | 15.6 | 4.2 | 3.9 | 51.9 | 48.5 | 878.3 | 840.9 |
| Stan dev | 1.0228548 | 0.6623274 | 0.8030308 | 0.5535261 | 1.5411 | 2.734641 | 81.21108 | 138.995 |
| T test | 5.034E−05 | | 0.0932204 | | 3.6E−06 | | 0.261787 | |

TABLE 17

| Trial map #: | YM99219 | | Comparison of Head Characteristics | | | | Maturity Date: | |
|---|---|---|---|---|---|---|---|---|
| Wet Date: | 12/10/ | Location: | Dome Valley | Ranch/lot: Monkey/6-A | | | 1 Icon | 3/24/ |
| Date evald: | 3/25/ | Grower: | Mission | Commercial Var Headmaster | | | 2 Spector | 3/24/ |

| Sample # | Core length (cm) | | Core diam. (cm) | | Head diam. (cm) | | Head length (cm) | |
|---|---|---|---|---|---|---|---|---|
| | Icon | Spector | Icon | Spector | Icon | Spector | Icon | Spector |
| 1 | 6.1 | 5.5 | 5.0 | 4.1 | 18.7 | 17.2 | 18.2 | 16.5 |
| 2 | 4.5 | 4.2 | 5.0 | 4.5 | 19.5 | 18.2 | 18.6 | 16.6 |
| 3 | 5.0 | 4.5 | 4.6 | 4.8 | 18.9 | 15.4 | 18.4 | 16.8 |
| 4 | 6.5 | 3.2 | 4.7 | 4.6 | 17.8 | 15.8 | 18.7 | 14.4 |
| 5 | 6.2 | 4.7 | 4.6 | 5.0 | 17.5 | 16.9 | 16.7 | 16.4 |
| 6 | 4.2 | 5.6 | 4.7 | 4.7 | 15.3 | 17.0 | 15.4 | 17.6 |
| 7 | 6.0 | 6.0 | 4.9 | 4.7 | 18.0 | 15.9 | 17.4 | 15.0 |
| 8 | 4.0 | 4.2 | 4.3 | 4.3 | 17.5 | 14.9 | 18.0 | 16.7 |
| 9 | 5.8 | 5.5 | 5.0 | 4.9 | 17.4 | 16.0 | 15.0 | 16.0 |

TABLE 17-continued

| Trial map #: | YM99219 | | | Comparison of Head Characteristics | | Maturity Date: | |
|---|---|---|---|---|---|---|---|
| Wet Date: | 12/10/ | Location: | Dome Valley | Ranch/lot: Monkey/6-A | | 1 Icon | 3/24/ |
| Date evald: | 3/25/ | Grower: | Mission | Commercial Var Headmaster | | 2 Spector | 3/24/ |
| 10 | 5.4 | 6.2 | 4.8 | 5.2 | 18.1 | 17.5 | 19.7 | 16.3 |
| 11 | 6.2 | 4.0 | 5.0 | 4.2 | 19.1 | 14.7 | 16.5 | 16.1 |
| 12 | 5.4 | 4.1 | 4.7 | 4.5 | 17.7 | 16.0 | 18.0 | 15.2 |
| 13 | 5.2 | 6.0 | 4.5 | 4.5 | 14.4 | 17.5 | 15.6 | 14.0 |
| 14 | 5.7 | 5.2 | 5.5 | 5.1 | 18.2 | 16.2 | 16.7 | 16.2 |
| 15 | 5.6 | 4.4 | 3.6 | 4.5 | 20.6 | 19.3 | 16.1 | 18.0 |
| 16 | 4.9 | 3.0 | 4.3 | 4.2 | 17.4 | 13.5 | 16.7 | 16.5 |
| 17 | 4.8 | 3.2 | 4.7 | 4.7 | 14.7 | 16.5 | 15.7 | 15.2 |
| 18 | 4.2 | 5.6 | 4.5 | 4.2 | 17.5 | 18.9 | 17.4 | 17.7 |
| 19 | 3.5 | 5.0 | 4.4 | 4.0 | 18.7 | 17.0 | 16.5 | 15.7 |
| 20 | 5.5 | 6.0 | 4.3 | 4.7 | 16.2 | 18.7 | 15.5 | 16.7 |
| 21 | 4.9 | 5.7 | 4.6 | 4.7 | 18.2 | 18.0 | 16.4 | 16.9 |
| 22 | 5.7 | 4.5 | 4.5 | 4.6 | 16.1 | 17.3 | 16.4 | 16.8 |
| 23 | 3.9 | 4.7 | 4.4 | 4.2 | 15.5 | 16.9 | 16.0 | 14.7 |
| 24 | 3.0 | 4.9 | 4.9 | 4.5 | 18.4 | 16.3 | 17.3 | 15.3 |
| Average | 5.1 | 4.8 | 4.6 | 4.6 | 17.6 | 16.7 | 17.0 | 16.1 |
| Stan dev | 0.9273228 | 0.935056 | 0.363532 | 0.316113 | 1.523987 | 1.378615 | 1.22047 | 1.0286388 |
| T test | 3.34E-01 | | 3.78E-01 | | 5.53E-02 | | 1.58E-02 | |

| | Avg Head Diameter (cm) | | Avg Head Diam: Core | | Frame diam (cm) | | Head wt. (g) | |
|---|---|---|---|---|---|---|---|---|
| Sample # | Icon | Spector | Icon | Spector | Icon | Spector | Icon | Spector |
| 1 | 18.5 | 16.9 | 3.0 | 3.1 | 55 | 51 | 1825 | 1298 |
| 2 | 19.1 | 17.4 | 4.2 | 4.1 | 54 | 56 | 1223 | 1266 |
| 3 | 18.7 | 16.1 | 3.7 | 3.6 | 52 | 51 | 1643 | 1396 |
| 4 | 18.3 | 15.1 | 2.8 | 4.7 | 51 | 50 | 1591 | 1221 |
| 5 | 17.1 | 16.7 | 2.8 | 5.2 | 52 | 54 | 1168 | 1264 |
| 6 | 15.4 | 17.3 | 3.7 | 3.7 | 56 | 53 | 1382 | 790 |
| 7 | 17.7 | 15.5 | 3.0 | 2.8 | 52 | 53 | 1256 | 1389 |
| 8 | 17.8 | 15.8 | 4.4 | 2.6 | 58 | 52 | 1499 | 1316 |
| 9 | 16.2 | 16.0 | 2.8 | 3.8 | 55 | 58 | 1077 | 1921 |
| 10 | 18.9 | 16.9 | 3.5 | 3.1 | 49 | 53 | 1008 | 1378 |
| 11 | 17.8 | 15.4 | 2.9 | 2.5 | 57 | 54 | 1673 | 1231 |
| 12 | 17.9 | 15.6 | 3.3 | 3.9 | 55 | 54 | 1168 | 1316 |
| 13 | 15.0 | 15.8 | 2.9 | 3.8 | 56 | 54 | 1827 | 1080 |
| 14 | 17.5 | 16.2 | 3.1 | 2.7 | 57 | 53 | 1839 | 876 |
| 15 | 18.4 | 18.7 | 3.3 | 3.6 | 55 | 53 | 1778 | 1665 |
| 16 | 17.1 | 15.0 | 3.5 | 3.4 | 50 | 50 | 1843 | 1431 |
| 17 | 15.2 | 15.9 | 3.2 | 5.0 | 56 | 46 | 1432 | 1102 |
| 18 | 17.5 | 18.3 | 4.2 | 3.3 | 56 | 50 | 1584 | 1338 |
| 19 | 17.6 | 16.4 | 5.0 | 3.3 | 57 | 50 | 1763 | 1057 |
| 20 | 15.9 | 17.7 | 2.9 | 3.0 | 56 | 50 | 1724 | 1386 |
| 21 | 17.3 | 17.5 | 3.5 | 3.1 | 58 | 54 | 1604 | 1407 |
| 22 | 16.3 | 17.1 | 2.9 | 3.8 | 59 | 52 | 1388 | 1193 |
| 23 | 15.8 | 15.8 | 4.0 | 3.4 | 47 | 54 | 1931 | 812 |
| 24 | 17.9 | 15.8 | 6.0 | 3.2 | 50 | 53 | 1541 | 1023 |
| Average | 17.3 | 16.4 | 3.5 | 3.5 | 54.3 | 52.4 | 1532.0 | 1256.5 |
| Stan dev | 1.1887436 | 0.9884638 | 0.7960187 | 0.7057176 | 3.182549794 | 2.430185 | 271.0698 | 252.0304 |
| T test | 1.25E-02 | | 9.86E-01 | | 2.64E-02 | | 6.76E-04 | |

TABLE 18

| Block: | 2 | Date Eval: | 8/24/ | | | |
|---|---|---|---|---|---|---|
| Variety: | Icon | Eval By: | dg/ndv | | | |
| | | Wet Date: | 5/11/ | | | |
| Plant number | Icon | Pybas 251 | Spector | Icon | Pybas 251 | Spector |
| 1 | 119 | 118 | 91 | 39 | 37 | 34 |
| 2 | 104 | 124 | 92 | 47 | 40 | 32 |
| 3 | 100 | 120 | 93 | 40 | 37 | 36 |
| 4 | 103 | 118 | 93 | 35 | 44 | 30 |
| 5 | 116 | 121 | 92 | 34 | 34 | 31 |
| 6 | 109 | 117 | 85 | 40 | 36 | 31 |
| 7 | 113 | 110 | 91 | 31 | 38 | 35 |
| 8 | 118 | 114 | 96 | 30 | 43 | 28 |
| 9 | 122 | 119 | 90 | 33 | 43 | 32 |
| 10 | 106 | 109 | 90 | 36 | 33 | 31 |
| 11 | 110 | 110 | 94 | 41 | 31 | 32 |

TABLE 18-continued

| Block: | 2 | | Date Eval: | 8/24/ | | |
| --- | --- | --- | --- | --- | --- | --- |
| | | | Eval By: | dg/ndv | | |
| Variety: | Icon | | Wet Date: | 5/11/ | | |
| 12 | 115 | 116 | 97 | 37 | 30 | 28 |
| 13 | 119 | 112 | 97 | 41 | 30 | 25 |
| 14 | 104 | 118 | 89 | 33 | 27 | 29 |
| 15 | 106 | 118 | 89 | 40 | 29 | 33 |
| 16 | 110 | 116 | 94 | 40 | 26 | 28 |
| 17 | 110 | 118 | 101 | 43 | 28 | 32 |
| 18 | 110 | 119 | 94 | 49 | 30 | 29 |
| 19 | 103 | 123 | 95 | 37 | 22 | 30 |
| 20 | 104 | 121 | 92 | 41 | 34 | 28 |
| Average | 110.05 | 117.05 | 92.75 | 38.35 | 33.6 | 30.7 |
| Standard Dev | 6.402919 | 4.2112006 | 3.522484 | 4.934039 | 6.107803 | 2.696977 |
| T-Test* | | 0.00191537 | 5.85E−10 | | 0.02813 | 0.04113 |

| Bolting Date | | | |
| --- | --- | --- | --- |
| | Icon | Pybas 251 | Spector |
| | 7/9/ | 7/7/ | 7/13/ |
| Days to Maturity | 59 | 57 | 63 |

| Bolting Leaves Shape: Straight or curved | | | |
| --- | --- | --- | --- |
| | Icon | Pybas 251 | Spector |
| | Curved | Curved | Curved |

| Margin Smooth or Dentate | | | |
| --- | --- | --- | --- |
| | Icon | Pybas 251 | Spector |
| | Dentate | Dentate | Dentate |

| Color Lt. Med. Dark | | | |
| --- | --- | --- | --- |
| | Icon | Pybas 251 | Spector |
| | Med | Med | Med |

| Terminal Inflorescence Yes, No | | | |
| --- | --- | --- | --- |
| | Icon | Pybas 251 | Spector |
| | Yes | Yes | Yes |

| Seed Color | | | |
| --- | --- | --- | --- |
| | Icon | Pybas 251 | Spector |
| | Black | Black | White |

| Bolting Habit | Icon | Pybas 251 | Spector |
| --- | --- | --- | --- |
| Lateral shoots btwn head and seed stalk | Yes | Yes | Yes |
| Lateral shoots above seed head | yes | Yes | Yes |
| Basal shoots | No | No | No |

The data presented in Tables 1–18 illustrate that Icon is a distinct and novel iceberg lettuce variety.

XI. STATEMENT OF DISTINCTNESS

Icon is distinguished primarily by type and adaptability. Icon is a Salinas type iceberg lettuce that performs well during the mid winter slot in Yuma, Ariz., where a Salinas type variety does not typically perform well. While other similar looking varieties bum and produce open and puffy heads, Icon is consistently uniform, solid heading and free of tip burn. When compared to the other varieties with this same adaptability, Icon is darker green, larger heading, larger framed and a much more uniform product.

Icon most closely resembles the variety Desert Spring. In Yuma large plantings of each variety were planted together. In the evaluation of these blocks, Icon was distinct from Desert Spring by the following characteristics:

1. Icon has a consistently larger head diameter.
2. Icon a consistently larger frame diameter.
3. Icon has a consistently heavier head weight.
4. Icon has a darker leaf color.

When compared to the seed bearing parent variety Pybas 251, Icon is distinct by the following characteristics:

Adaptability: Icon is best adapted for winter desert plantings.

Head Size: Icon has a smaller head size.

Color: Icon has a darker leaf color.

The main distinction between Icon and Pybas 251 is the adaptability. The primary planting slot for Icon is during the second half of November in Yuma Ariz. where it produces a larger and more uniform head size than any of the existing varieties for the same slot. The variety Pybas 251 is primarily slotted for late winter and early spring plantings in the Salinas Valley. Icon when planted in the Salinas Valley during this time has an inconsistent performance as it can be puffy or very loose heading.

Though the statistical measurements are similar, they do not reflect the field performance. Pybas 251 when grow during the same period in Yuma as Icon, will be large and puffy, and show tip burn much more readily.

When compared to the pollen bearing parent, Spector, Icon is significantly larger heading and framed, and generally produces a longer core as an indication of its tendency to be typically 2–3 days earlier maturing. Icon will produce a large marketable head during the winter period where Spector will struggle to make size.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

We claim:

1. Lettuce seed having ATCC Accession Number PTA-4011.
2. A lettuce plant produced by growing the seed of claim 1.
3. A lettuce plant having all the physiological and morphological characteristics of the lettuce plant of claim 2.
4. A method of making an $F_1$ hybrid lettuce plant consisting of crossing Icon as a first lettuce parent plant with a second lettuce parent plant, wherein Icon is grown from the seed of claim 1; harvesting the resultant $F_1$ hybrid seed; and growing an $F_1$ hybrid seed into an $F_1$ hybrid lettuce plant.
5. Pollen of the plant of claim 2.
6. An ovule of the plant of claim 2.
7. Tissue culture of the plant of claim 2.

* * * * *